US008568286B2

(12) United States Patent  
Sih et al.

(10) Patent No.: US 8,568,286 B2  
(45) Date of Patent: Oct. 29, 2013

(54) METHODS TO POSITION THERAPEUTIC AGENTS USING A MAGNETIC FIELD

(75) Inventors: Haris J. Sih, Minneapolis, MN (US); Craig Stolen, New Brighton, MN (US); Jihong Ou, Maple Grove, MN (US); Darrell O. Wagner, Isanti, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1122 days.

(21) Appl. No.: 11/424,107

(22) Filed: Jun. 14, 2006

(65) Prior Publication Data

US 2008/0006281 A1   Jan. 10, 2008

(51) Int. Cl.  
*A61N 2/00* (2006.01)

(52) U.S. Cl.  
USPC .............................. 600/12; 600/11; 128/899

(58) Field of Classification Search  
USPC ...................... 128/897–899; 607/9; 600/9–15  
See application file for complete search history.

(56) References Cited

U.S. PATENT DOCUMENTS

| | | | | |
|---|---|---|---|---|
| 4,106,488 A | * | 8/1978 | Gordon | 424/1.37 |
| 4,345,588 A | * | 8/1982 | Widder et al. | 600/12 |
| 5,271,400 A | * | 12/1993 | Dumoulin et al. | 600/410 |
| 5,549,915 A | * | 8/1996 | Volkonsky et al. | 424/490 |
| 5,727,553 A | * | 3/1998 | Saad | 600/407 |
| 5,830,207 A | * | 11/1998 | Leeb et al. | 604/890.1 |
| 5,843,633 A | * | 12/1998 | Yin et al. | 435/2 |
| 5,902,238 A | * | 5/1999 | Golden et al. | 600/424 |
| 5,921,244 A | * | 7/1999 | Chen et al. | 128/897 |
| 6,099,460 A | * | 8/2000 | Denker | 600/17 |
| 6,315,709 B1 | * | 11/2001 | Garibaldi et al. | 600/12 |
| 6,475,753 B1 | * | 11/2002 | Ruben et al. | 435/69.1 |
| 6,739,342 B1 | * | 5/2004 | Fredriksson et al. | 128/899 |
| 2002/0133115 A1 | * | 9/2002 | Gordon et al. | 604/96.01 |
| 2003/0082148 A1 | * | 5/2003 | Ludwig et al. | 424/93.7 |
| 2003/0180267 A1 | * | 9/2003 | Harrington et al. | 424/93.21 |
| 2004/0138552 A1 | * | 7/2004 | Harel et al. | 600/407 |
| 2006/0057211 A1 | * | 3/2006 | Chorny et al. | 424/486 |
| 2006/0142632 A1 | * | 6/2006 | Meretei | 600/12 |
| 2006/0228421 A1 | * | 10/2006 | Seeney et al. | 424/489 |
| 2007/0003528 A1 | * | 1/2007 | Consigny et al. | 424/93.7 |
| 2007/0231393 A1 | * | 10/2007 | Ritter et al. | 424/489 |
| 2008/0019917 A1 | * | 1/2008 | Pacey | 424/9.3 |

OTHER PUBLICATIONS

McKinney-Freeman S, Jackson K, Camargo F, Ferrari G, Mavilio F, Goodell M. Muscle-derived hematopoietic stem cells are hematopoietic in origin. PNAS 99(3): 1341-1346, Feb. 5, 2002.*

Margolis L, Namiot V, Kijukin L. Magnetoliposomes: Another Principle of Cell Sorting. Biochimica et Biophysica Acta 735: 193-195, 1983.*

Bulte J, Douglas T, Witwer B, Zhang S, Strable E, Lewis B, Zywicke H, Miller B, van Gelderen P, Moskowitz B, Duncan I, Frank J. Magnetodendrimers allow endosomal magnetic labeling and in vivo tracking of stem cells. Nature Biotechnology 19: 1141-1147, Dec. 2001.*

(Continued)

*Primary Examiner* — Charles A Marmor, II  
*Assistant Examiner* — Catherine E Burk  
(74) *Attorney, Agent, or Firm* — Schwegman Lundberg & Woessner, P.A.

(57) ABSTRACT

A system for controlling the location of a therapeutic agent administered to a mammal is provided. The system employs a device that is capable of generating a magnetic field and a therapeutic agent labeled with a magnetically responsive moiety. Methods which employ the device and the therapeutic agent are also provided.

12 Claims, 6 Drawing Sheets

(56) References Cited

OTHER PUBLICATIONS

Kubo T, Sugita T, Shimose S, Yasuaki N, Ikuta Y, Murakami T. Targeted delivery of anticancer drugs with intravenously administered magnetic liposomes in osteosarcoma-bearing hamsters. International Journal of Oncology 17: 309-315, 2000.*

Arbab A, Jordan E, Wilson L, Yocum G, Lewis B, and Frank J. In Vivo Trafficking and Targeted Delivery of Magnetically Labeled Stem Cells. Human Gene Therapy 15:351-360, Apr. 2004.*

Qian ZM, Li H, Sun H, Ho K. Targeted Drug Delivery via the Transferrin Receptor-Mediated Endocytosis Pathway. Pharmacological Reviews 54: 561-587, 2002.*

Bulte, J. W., et al., "Magnetodendrimers allow endosomal magnetic labeling and in vivo tracking of stem cells", *Nature Biotechnology*, 19(12), (Dec. 2001), 1141-7.

Condon, G., "Magnet to the Heart New Catheter-Guiding Technology Helping Make Cardiac Repairs Easier, Sater", *The Hartford Courant*, (Mar. 29, 2005), 3 pgs.

Li, W., et al., "Magnetic Nanobeads for Local Gene Delivery: A Novel Vector for Myocardial Therapy", *Circulation*, 112(17), (Abstract Only), (2005), p. II-126.

O'Riordan, M., "Remote magnetic navigation safe and feasible for AF ablation", theheart.org, [online]. Retrieved via the Internet: <URL: http://www.theheart.org/article/615529.do>, (Dec. 6, 2006), 2 pgs.

* cited by examiner

METHODS TO POSITION THERAPEUTIC AGENTS USING A MAGNETIC FIELD

FIELD OF THE INVENTION

This document relates generally to therapy of living tissue including cell, protein or drug therapy, and particularly, but not by way of limitation, to method and apparatus for regulation of the location of cell, protein or drug in a mammal via a magnetic field.

BACKGROUND

The heart is the center of a person's circulatory system. It includes an electromechanical system performing two major pumping functions. The heart includes four chambers: right atrium (RA), right ventricle (RV), left atrium (LA), and left ventricle (LV). The left portions of the heart, including LA and LV, draw oxygenated blood from the lungs and pump it to the organs of the body to provide the organs with their metabolic needs for oxygen. The right portions of the heart, including RA and RV, draw deoxygenated blood from the body organs and pump it to the lungs where the blood gets oxygenated. The efficiency of the pumping functions, indicative whether the heart is normal and healthy, is indicated by measures of hemodynamic performance, such as parameters related to intracardiac blood pressures and cardiac output.

In a normal heart, the sinoatrial node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction and/or deteriorated myocardial tissue cause dysynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulting from cardiac ischemia, a condition in which the myocardium is deprived of adequate oxygen and metabolite removal due to an interruption in blood supply. The adult heart lacks a substantial population of precursor, stem cells, or regenerative cells. Therefore, after MI, the heart lacks the ability to effectively regenerate cardiomyocytes to replace the injured cells in the infarcted areas of the myocardium. Each injured area eventually becomes a fibrous scar that is non-conductive and non-contractile. Consequently, the overall contractility of the myocardium is weakened, resulting in decreased cardiac output. As a physiological compensatory mechanism that acts to increase cardiac output in response to MI, the LV diastolic filling pressure increases as the pulmonary and venous blood volume increases. This increases the LV preload (stress on the LV wall before it contracts to eject blood). One consequence is the progressive change of the LV shape and size, a process referred to as remodeling. Remodeling is initiated in response to a redistribution of cardiac stress and strain caused by the impairment of contractile function in the infarcted tissue as well as in nearby and/or interspersed viable myocardial tissue with lessened contractility due to the infarct. The remodeling starts with expansion of the region of the infarcted tissue and progresses to a chronic, global expansion in the size and change in the shape of the entire LV. Although the process is initiated by the compensatory mechanism that increases cardiac output, the remodeling ultimately leads to further deterioration and dysfunction of the myocardium. Consequently, post MI patients experience impaired hemodynamic performance and have a significantly increased risk of developing heart failure.

It has been proposed that cardiac transfer of bone marrow cells (BMCs) can be used for cardiac tissue repair and regeneration in patients after acute MI (AMI) (Strauer et al., *Circulation*, 106:1913 (2002); Assmus et al., *Circulation*, 106: 3009 (2002); Wollert et al., *Circ. Res.*, 96:151 (2005)). This concept is supported by the recent randomized controlled bone marrow transfer to enhance ST-elevation infarct regeneration trial (BOOST), showing that intracoronary transfer of unselected autologous BMCs during the early postinfarction period enhances recovery of left ventricular (LV) ejection fraction after 6 months (Wollert et al., *Lancet.*, 364:141 (2004)). The mechanisms by which BMCs enhance functional recovery after AMI remain poorly understood. Regardless, BMC homing in the infarcted myocardium is likely an important early event after intracoronary transfer. In animal models, myocardial homing of transplanted stem and progenitor cells has been monitored by fluorescence or radioactive labeling (Kocher et al., *Nat. Med.*, 7:430 (2001); Aicher et al., *Circulation*, 107:2134 (2003); Brenner et al., *J. Nucl. Med.*, 45:512 (2004)). However, stem cell transplantation for MI repair is hindered by low levels of cell retention immediately post-transplant. For instance, Hofmann et al. (*Circ.*, 111:2198 (2005)) report that after intracoronary transfer of $^{18}$F-FDG-labeled CD34-enriched cells, 14% to 39% of the total activity was detected in the infarcted myocardium. Hayashi et al. (*Cell Transplant.*, 13:639 (2004)) disclose that while 16% of transplanted cells were found within 1 day after intramyocardial injection, other methods of cell delivery yielded levels of retention <5%.

Thus, there is a need for methods and apparatus to improve donor cell retention in vivo.

SUMMARY

The invention provides methods, systems and devices for enhancing cell, protein or drug therapies by increasing cell, protein or drug retention via an internally or externally applied magnetic field. Prior to administration, cells, protein or drug are labeled ex vivo with a force responsive moiety, such as a complex having a metal, a metal binding protein complexed with a metal, or other molecule, e.g., a buckyball (hollow spheres made up of pentagons or hexagons of fullerene), that is responsive to an internally or externally applied magnetic field.

In one embodiment, the invention provides for a system having a device that is capable of generating a magnetic field which may be employed to control the location of therapeutic agents including exogenously administered biologic agents such as donor cells or isolated proteins, or drugs, labeled with a force responsive moiety. The system includes an external device or an implantable device capable of generating a magnetic field. The device can thus be used to regulate the local concentration of exogenously administered labeled cells, proteins or drugs, thereby providing an enhanced therapeutic effect. For instance, harvested autologous cells, isolated protein or drug are labeled ex vivo with a magnetic moiety, e.g., labeled with a complex having a metal, e.g., a magnetodendrimer or a magnetic bead, including coated or impregnated beads, such as iron-dextran beads or iron-polysaccharide beads, for instance, iron-alginate beads, or an antibody coupled to a force responsive moiety. In one embodiment, donor cells are labeled ex vivo with a metal or a complex having a metal, e.g., an antibody coated on or conjugated to (covalently attached to) a metal containing bead, via phagocytosis, liposome-mediated transfection, endocytosis or passive uptake. For instance, donor cells are contacted with a magnetodendrimer, which is taken up into the cells. In another embodiment, donor cells are labeled ex vivo with an antibody specific for a cell surface molecule covalently linked to a metal or a complex having a metal. In one embodiment, the antibody is linked to a biodegradable magnetic bead. In yet another embodiment, donor cells are recombinant donor cells that express, e.g., overexpress, a metal binding protein, which recombinant cells are optionally contacted with a selected metal ex vivo. In a further embodiment, donor cells are recombinant donor cells that express, e.g., overexpress, a synthetic (nonnatural) open reading frame which encodes a charged gene product. In one embodiment, isolated protein or drug is covalently linked to a force responsive moiety or a complex having a force responsive moiety. In another embodiment, isolated protein or drug is bound by an antibody which is associated with a force responsive moiety. In yet another embodiment isolated protein or drug is embedded in or coated on, or both, a complex having a force responsive moiety, for instance, embedded in or coated on, or both, a magnetic bead such as a buckyball.

The labeled therapeutic agent may be administered to a mammal by any route or means, e.g., intravenously via a catheter or needle. After and/or during therapeutic agent administration, a magnetic field is locally applied to a target area in the mammal. The longer a labeled donor cell remains in a target area, the greater the opportunity for natural engrafting, leading to an increase in the number of engrafted cells, which in turn may provide a desirable effect such as improved tissue function or a healing response. Likewise, the longer a therapeutic protein or drug remains in a target area, the greater the opportunity for a similar or an enhanced therapeutic effect, e.g., with a lower amount of administered protein or drug relative to systemic or other local means of administration.

For example, an implantable device that is capable of generating a magnetic field, such as a lead having a electromagnet or magnet, may be employed to generate a magnetic field that is applied in an amount and/or for a time which results in localization of the force responsive moiety associated with the therapeutic agent in a mammal. In another embodiment, the device is an external device that is capable of generating a magnetic field, which field, when applied to a selected physiological site of a mammal administered a therapeutic agent labeled with a force responsive moiety, enhances the localization of the labeled therapeutic agent. Once the field is no longer applied (turned off or the device is physically withdrawn), the amount of therapeutic agent at the targeted physiological site may decrease, e.g., the therapeutic agent may enter the circulation or be otherwise decreased in local concentration, or remain substantially the same as during field application for a period of time. The field may be reapplied to the same or a different physiological site, or both, for one or more periods of time. The present invention thus provides spatial and temporal control of therapeutic agents via an implantable or external device. The labeled therapeutic agents and devices of the invention may be employed to prevent, inhibit or treat at least one symptom of a particular condition or disease in a mammal, e.g., conditions or diseases including but not limited to myocardial infarction, heart failure, liver failure, neurodegenerative diseases and diabetes.

Accordingly, the invention provides a system for control of therapeutic agent delivery, having: a magnetic field generating device adapted to generate a magnetic field which regulates a force responsive moiety; and a composition having a therapeutic agent associated with a complex which has a force responsive moiety that is responsive to the magnetic field. In one embodiment, the complex is biocompatible, biodegradable, or both.

The invention also provides methods for spatial and temporal localization of a therapeutic agent in a mammal. The method includes providing a mammal having a therapeutic agent labeled with a force responsive moiety. In one embodiment, the force responsive moiety labeled therapeutic agent is encapsulated in a liposome or other delivery vehicle prior to administration. In another embodiment, the therapeutic agent is coated on or encapsulated in, or both, a micro- or nanoparticle. In one embodiment, to increase the local concentration of a therapeutic protein, the protein is contacted ex vivo with an antibody specific for the protein which antibody is associated with a force responsive moiety or the protein is linked, via a linker such as a cleavable linker, to a metal chelator, or to a magnetic bead or other force responsive complex. In one embodiment, at least the nontherapeutic agent portion of the labeled therapeutic agent is biocompatible, biodegradable, or both. In one embodiment, the labeled therapeutic agent is systemically administered to the mammal, and a magnetic field is applied to the mammal in a selected physiological site, e.g., near the heart. The application of the field is in an amount and for a time effective to increase the amount (concentration) of labeled therapeutic agent at the physiological site.

In one embodiment, the invention provides a method to enhance the efficacy of a therapeutic agent. The method includes administering to a mammal in need of therapy a composition comprising a therapeutic agent associated with a complex which comprises a force responsive moiety that is responsive to a magnetic field. A magnetic field is applied to the mammal at a selected physiological site in an amount effective to increase the amount of the therapeutic agent at the physiological site. In one embodiment, the mammal is a human. The mammal may be in need of myocardial repair, or have liver failure, a neurodegenerative disease, diabetes or other condition. In one embodiment, the therapeutic agent comprises a biologic agent, for instance, a biologic agent including donor cells, e.g., stem cells, recombinant cells such as recombinant donor cells including an expression cassette comprising a promoter operably linked to an open reading frame encoding a force responsive gene product. In one embodiment, the donor cells include magnetic nanoparticles. In one embodiment, the donor cells are bound to antibodies having the force responsive moiety. In one embodiment, the biologic agent includes isolated protein, e.g., isolated protein covalently linked to the force responsive moiety. In one embodiment, the composition comprises a drug covalently linked to the complex. The complex may include a bead. The composition may be locally or systemically administered. The field may be applied via any device, for instance, via an implanted lead, an implanted stylet, or an external device.

Further provided is a method for spatial and temporal localization of recombinant donor cells which express an open reading frame for a force responsive gene product. The method includes delivering (administering) to a mammal recombinant cells having a vector expressing a force responsive gene product, e.g., an expression cassette having a promoter operably linked to an open reading frame for a metal binding protein optionally in conjunction with a metal, and applying a magnetic field to a physiological site in the mammal, thereby regulating the location of the recombinant cell. In one embodiment, the expression cassette contains a heterologous promoter. Exemplary classes of metal binding proteins include ferritin proteins, transferrin receptor proteins, iron regulatory proteins, and iron scavenger proteins, such as proteins that are substantially homologous to wild type metal binding proteins. In another embodiment, the recombinant cells have a vector encoding a synthetic gene product with a charge that is greater than the average charge of proteins in the cell.

The systems and methods of the invention may be employed to inhibit or treat any condition or disease in a mammal such as a human, diseases including but not limited to myocardial damage, liver failure, neurodegenerative diseases, diabetes, or other diseases that can be treated by administration of therapeutic agents that are labeled by a force responsive moiety. While particular conditions, therapeutic agents and force responsive moieties are described herein, the invention is not limited to any particular condition, therapeutic agent or force responsive moiety.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION OF THE INVENTION

Definitions

Figure 1:
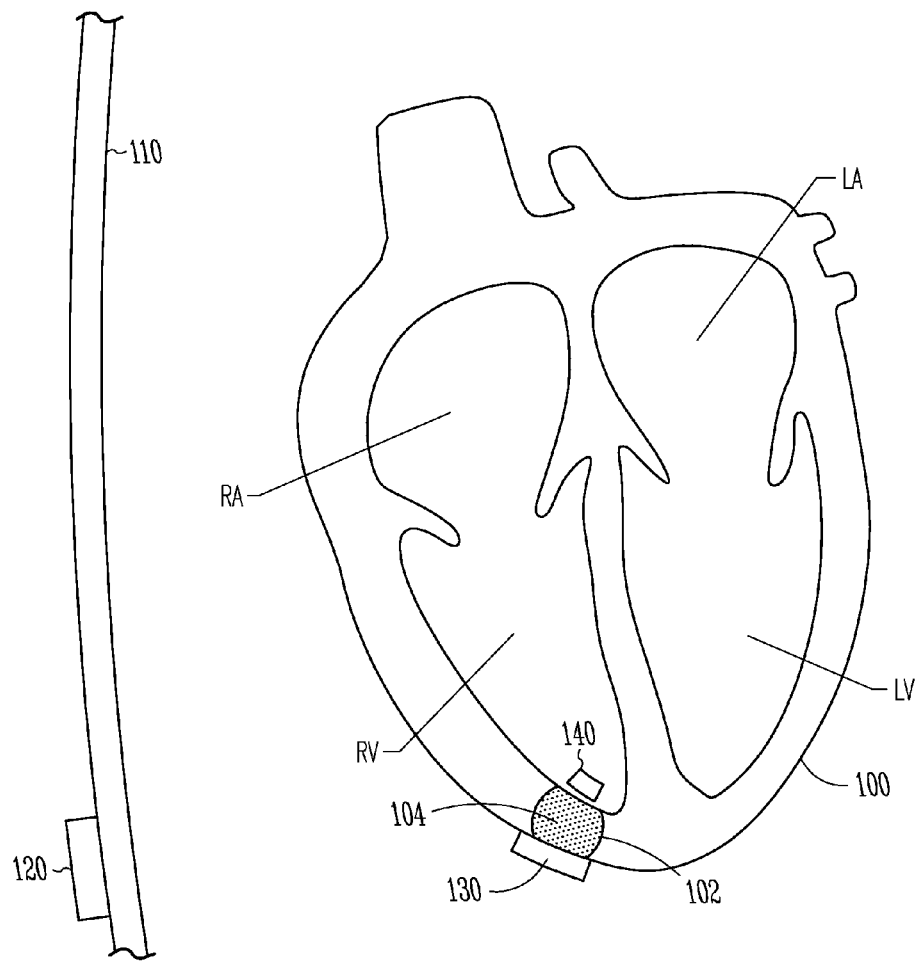
FIG. 1 is an illustration of an embodiment of a therapy delivery system including one or more magnetic field generating devices and portions of the environment in which the therapy system operates.

A "metallodendrimer" includes metal and dendrimers. Dendrimers are highly branched synthetic polymers that have three different building blocks-core, branching units and functional terminal groups. Metallodendrimers may be prepared by a variety of methods, some of which are described herein.

"Ferrous or ferric ion-containing material" includes a material such as a compound or molecule that includes a ferrous or ferric ion.

"Metal (oxyhydr)oxide" includes a metal oxide produced oxidation of a transition metal ion or a metal oxyhydroxide produced by hydrolysis of a lanthanide metal ion.

"Metal (oxyhdr)oxide-dendrimer composition" refers generically to, and is inclusive of, complexes, aggregates, nanocomposites or aqueous suspensions.

A "paramagnetic metal" refers to a metal with unpaired electrons. Suitable paramagnetic metals include transition elements and lanthanide series inner transition elements. Additional suitable paramagnetic metals include, e.g., Yttrium (Y), Molybdenum (Mo), Technetium (Tc), Ruthenium (Ru), Rhodium (Rh), Tungsten (W), and Gold (Au). Additional specific suitable specific paramagnetic metals include, e.g., Y(III), Mo(VI), Tc(IV), Tc(VI), Tc(VII), Ru(III), Rh(III), W(VI), Au(I), and Au(III).

A "lanthanide," "lanthanide series element" or "lanthanide series inner transition element" refers to Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), or Lutetium (Lu). Specific suitable lanthanides include, e.g., Ce(III), Ce(IV), Pr(III), Nd(III), Pm(III), Sm(II), Sm(III), Eu(II), Eu(III), Gd(III), Tb(III), Dy(III), Ho(III), Er(III), Tm(III), Yb(II), Yb(III), and Lu(III).

A "first row transition metal" refers to Calcium (Ca), Scandium (Sc), Titanium (Ti), Vanadium (V), Chromium (Cr), Manganese (Mn), Iron (Fe), Cobalt (Co), Nickel (Ni), Copper (Cu), or Zinc (Zn). Specific first row transition metals include, e.g., Sc(III), Ti(II), Ti(III), Ti(IV), V(II), V(III), V(IV), V(V), Cr(II), Cr(III), Cr(VI), Mn(II), Mn(III), Mn(IV), Mn(VII), Fe(II), Fe(III), Co(II), Co(III), Ni(II), Ni(III), Cu(I), Cu(II), and Zn(II).

The term "biocompatible" as used herein is intended to describe compounds or complexes that are generally not toxic to cells. Compounds or complexes are "biocompatible" if their addition to cells in vitro results in less than or equal to about 30%, 20%, 10%, 5%, or 1% cell death and does not substantially induce inflammation or other such unwanted adverse effects in vivo.

As used herein, "biodegradable" compounds or complexes are those that, when introduced into cells, are broken down by the cellular machinery into components without a significant toxic effect on the cells (i.e., fewer than about 30%, 20%, 10%, 5%, or 1% of the cells are killed).

When two or more moieties or molecules are "associated with" one another, they are linked by a direct or indirect covalent or non-covalent interaction. Non-covalent interactions include, but are not limited to, hydrogen bonding, van der Waals interactions, hydrophobic interactions, magnetic interactions, electrostatic interactions, and the like.

Examples of chelating groups include: a residue of a polyaminopolycarboxylic acid and the derivatives thereof, in particular selected from ethylenediaminotetraacetic acid (EDTA), diethylenetriaminopentaacetic acid (DTPA), 1,4,7,10-tetraazacyclododecane-1,4,7,10-etraacetic acid (DOTA), 1,4,7,10-tetraazacyclododecane-1,4,7-triacetic acid (DO3A), 10-(2-hydroxypropyl)-1,4,7,10-tetraazacyclododecane-1,4,7-triacetic acid (HPDO3A), 4-carboxy-5,8,11-tris(carboxymethyl)-1-phenyl-2-oxa-5,8,11-triazatridecan-13-oic acid (BOPTA), N-[2-[bis-(carboxymethyl)amino]-3-(4-ethoxyphenyl)propyl]-N-[2-[bis(carboxymethyl)amino]ethyl]glycine (EOB-DTPA), N,N-bis[2-(carboxymethyl)[(methylcarbamoyl)methyl]amino]ethyl]glycine (DTPA-BMA), 2-methyl-1,4,7,10-tetraazacyclododecane-1,4,7,10-tetraacetic acid (MCTA), (α,α',α", α''')-tetramethyl-1,4,7,10-tetraazacyclododecane-1,4,7,10-tetracetic acid (DOTMA); the residue of a polyaminophosphonic acid ligand and derivatives thereof, polyaminophosphinic acid and derivatives thereof, in particular ethylenedinitrilotetrakis(methylphosphonic) acid (EDTP); 1,4,7,10-tetraazacyclododecane-1,4,7,10-tetrakis[methylene(methylphosphonic)]acid and 1,4,7,10-etraazacyclododecane-1,4,7,10-tetrakis[methylene (methylphosphinic)]acid; the residue of macrocyclic chelants such as texaphyrins, porphyrins, phthalocyanines. See also Alexandar, *Chem. Rev.,* 95: 273 (1995), Jackals, *Pharm. Med. Imag.,* Section III, Chapter 20 (1990), Meyer et al., *Invest. Radiol.,* 25:553 (1990), and U.S. Pat. Nos. 5,155,215, 5,087, 440, 5,219,553, 5,188,816, 4,885,363, 5,358,704, and 5,262, 538, all of which are incorporated by reference herein.

"Endocytic transfection agent" encompasses any transfection agent that delivers a foreign molecule (such as DNA) or other material into a cell via endocytosis and/or diffusion through the cell membrane. Endocytic transfection agents are distinguished from biolistic transfection agents since biolistic transfection agents are projected into a cell via a ballistic device as opposed to endocytosis and/or diffusion.

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest for gene therapy. Vectors include, for example, recombinant viral vectors (such as recombinant adenoviruses, adeno-associated viruses (AAV), lentiviruses, herpesvirus and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described (see, e.g., Curiel et al., *Proc. Natl. Acad. Sci. USA,* 88:8850 (1991)).

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" or "recombinant cell" is meant a cell containing a transgene or otherwise manipulated by recombinant techniques, e.g., a cell having a gene "knockout". For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source, or to cells which have not been genetically modified, i.e., nonrecombinant cells. A wild-type gene is that which is most frequently observed in a population and is thus arbitrarily designated the "normal" or "wild-type" form of the gene. In contrast, the term "synthetic," "modified" or "mutant" refers to a gene or gene product that displays modifications in sequence and/or functional properties (i.e., altered characteristics) when compared to wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector, e.g., a replication-defective viral vector.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer element" is meant a nucleic acid sequence that, when positioned proximate to a promoter, confers increased transcription activity relative to the transcription activity resulting from the promoter in the absence of the enhancer domain. By "cardiac-specific enhancer element" is meant an element, which, when operably linked to a promoter, directs gene expression in a cardiac cell and does not direct gene expression in all tissues or all cell types. Cardiac-specific enhancers of the present invention may be naturally occurring or non-naturally occurring. One skilled in the art will recognize that the synthesis of non-naturally occurring enhancers can be performed using standard oligonucleotide synthesis techniques.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to molecules including a protein, nucleic acid, or cell refers to a protein or nucleic acid which has been introduced into a cell or organism by artificial or natural means, or in relation to a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide or polypeptide or cell refers to a nucleic acid sequence, peptide, polypeptide or cell that is identified and separated from at least one contaminant nucleic acid, polypeptide or other biologic component with which it is ordinarily associated in its natural source. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may be single-stranded), but may contain both the sense and antisense strands (i.e., the molecule may be double-stranded).

The term "recombinant DNA molecule" as used herein refers to a DNA molecule that is comprised of segments of DNA joined together by means of molecular biologic techniques.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished.

A "cytokine" is a relatively low molecular weight protein secreted by cells, e.g., cells of the immune system, for the purpose of altering the function(s) of those cells and/or adjacent cells. Cytokines include interleukins, e.g., molecules which regulate the inflammatory and immune response, as well as growth and colony stimulating factors.

The term "agents," as used in this document, include agents that are chemical and/or biologic in origin. A "biologic agent" includes agents that are derived (obtained) from wild-type mammalian cells, such as nonrecombinant mammalian cells in culture, e.g., protein, DNA, RNA, glycoprotein, proteoglycans, and the like. A "drug" as used herein is a nonbiologic agent.

"Cardiovascular" conditions or diseases include, but are not limited to, coronary artery disease/ischemia, coronary artery disease (CAD), ischemia, angina (chest pain), thrombosis, coronary thrombosis, myocardial infarction (MI), silent ischemia, stenosis/restenosis, transient ischemic attack (TIA), atherosclerosis, peripheral vascular disease, bradyarrhythmia, e.g., bradyarrhythmia, bradycardia, sick sinus rhythm (Sick Sinus Syndrome), sinus bradycardia, sinoatrial block, asystole, sinus arrest, syncope, first degree atrioventricular (AV) block, second degree atrioventricular (AV) block, third degree atrioventricular (AV) block, chronotropic incompetence, tachyarrhythmia, e.g., tachyarrhythmia, tachycardia, fibrillation, flutter, atrial fibrillation, atrial flutter, familial atrial fibrillation, paroxysmal atrial fibrillation, permanent atrial fibrillation, persistent atrial fibrillation, supraventricular tachyarrhythmias, sinus tachycardia, reentry (reentrant arrhythmias), AV nodal reentry, focal arrhythmia, ectopy, ventricular fibrillation (VF), ventricular tachycardia (VT), Wolff-Parkinson-White Syndrome (WPW) and sudden cardiac death, heart failure, e.g., heart failure, cardiomyopathy, congestive heart failure, hypertrophic cardiomyopathy, remodeling, non-ischemic cardiomyopathy, dilated cardiomyopathy, restrictive cardiomyopathy, diastolic heart failure, systolic heart failure, and chronic heart failure, heart block/electrical disorders, e.g., atrioventricular (AV) block, bundle branch block (BBB), left bundle branch block (LBBB), right bundle branch block (RBBB), Long QT Syndrome (LQTS), premature ventricular contraction (PVC), electrical remodeling, intraventricular conduction defect, and hemiblock, hemodynamic deficiency, e.g., hypertension, hypotension, left ventricular dysfunction, low ejection fraction, low cardiac output, and low stroke volume, sudden cardiac death, cardiac arrest, sudden cardiac death (SCD), ventricular fibrillation, and pump failure, as well as bacterial endocarditis, viral myocarditis, pericarditis, rheumatic heart disease, and syncope. In particular, a cardiovascular condition includes, but is not limited to, arrhythmia, e.g., atrial fibrillation, ventricular fibrillation or bradycardia, ischemia, heart failure and hyperplasia not associated with neoplastic disease, which condition may be associated with ventricular remodeling, diastolic dysfunction, aberrant body temperature, aberrant or altered pressure, e.g., altered venous, left ventricular or left atrial pressure, aberrant or altered heart rate or sounds, aberrant or altered electrogram, aberrant or altered cardiac metabolism, such as altered blood pH, glucose, $pO_2$, $pCO_2$, minute ventilation, creatine, CRP, Mef2A, creatine kinase or creatine kinase MB levels, aberrant or altered pulmonary or thoracic impedance, aberrant or altered stroke volume, aberrant or altered neurohormone levels, aberrant or altered electrical activity, aberrant or altered sympathetic nerve activity, aberrant or altered renal output, aberrant or altered filtration rate, aberrant or altered angiotensin II levels, or aberrant or altered respiratory sounds, and the like.

A "neurodegenerative" condition or disease includes but is not limited to Alzheimer's disease, multiple sclerosis, amyolateral sclerosis, Huntington's disease, spinocerebellar ataxis, Machado-Joseph disease, spinal or bulbar muscular atrophy, Parkinson's disease, Pick's disease, and spongiform encephalopathies, myotonic dystrophy, and the like.

Exemplary Therapeutic Agents

Agents within the scope of the invention include but are not limited to drugs and biologic agents such as cells or proteins, e.g., enzymes, hormones, cytokines, growth factors, receptor ligands, antibodies, antigens, ion binding compounds including crown ethers and other chelators, toxins, and the like. For instance suitable agents include cytokines such as erythropoietin (EPO), thrombopoietin (TPO), the inerleukins (including IL-1 through IL-17), insulin, insulin-like growth factors (including TGF-alpha and TGF-beta), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cortisol, estradiol, follicle stimulating hormone (FSH), thyroid-stimulating hormone (TSH), leutinizing hormone (LH), progesterone, testosterone, toxins including ricin, and any drugs as outlined in the *Physician's Desk Reference,* 2003 and the *Merck Index,* 12th Edition, both of which are incorporated by reference. In one embodiment, the drug may be an antineoplastic drug, including but not limited to alkylating agents such as alkyl sulfonates (busulfan, improulfan, piposulfan); aziridines (benzodepa, cargoquone, meturedepa, uredepa); ethylenimines and methylmelamines (altretamine, trethylenemelamine, triethylenephosporamide, triethylenethiophosphoramide, trimethylolmelamine); nitrogen mustards (chlorambucil, chlornaphazine, cyclophosphanmide, estramustine, ifosfamide, mechlorethamine, mechlorethamine oxide hydrochloride, melphalan, novemebichin, phenesterine, prednimustine, trofosfamide, uracil mustard; nitrosoureas (carmustine, chlorozotocin, fotenmustine, lomustine, nimustine, ranimustine); dacarbazine, mannomustine, mitobranitol, mitolactol; pipobroman; doxorubicin, and cisplatin (including derivatives).

In one embodiment, the drug is an antiviral or antibacterial drug, including but not limited to aclacinomycins, actinomycin, anthramycin, asaserine, bleomycins, cuctinomycin, carubicin, carzinophilin, chromomycins, ductinomycin, daunorubicin, 6-diazo-5oxn-1-norieucine, doxorubicin, epirubicin, mitomycins, mycophenolic acid, nogalumycin, olivomycins, peploymycin, plicamycin, porfiromycin, puromycin, streptonigrin, streptozocin, tubercidin, ubenimex, zinostatin, zorubicin; aminoglycosides and polyene and macrolide antibiotics.

In one embodiment, the drug is a radio-sensitizer drug.

In one embodiment, the drug is an anti-inflammatory drug (either steroidal or non-steroidal).

In one embodiment, drugs within the scope of the present subject matter include, but are not limited to anti-hypertensive agents, anti-arrhythmic agents, aldosterone antagonists, endothelin receptor antagonists, TNF-α inhibitors, e.g., etanercept, matrix metalloproteinase inhibitors, vasodilators, angiotensin receptor blockers, e.g., losartan or anomethyl substituted thiaxoliums, imidazoliums, thiaxoles, imidazole, oxazole, pentoxifylline, thalidomide, vasopressors, vasodilators, anti-hyperlipidemic agents, anti-anginal agents, ionotropic agents, diuretics, volume expanders, thrombolytics, antiplatelet agents, ouabain, amlodipine, pentaxifylline, amiodarone, SR33589 or ATI-2001 (Kodama, *Cardiovas. Res.,* 35:13 (1997)), adenosine, retinoic acid, glycolic acid, hydrazones, cyanomethyl substituted thiazoliums, imidazoliums, azolium chroman, thiazole, imidazole, pentafluorosulfanylbenzoyl guanidines, candesartan, PD 098059 or LY294002 (see Hafizi et al., *Cir. Exp. Pharma Physiol.,* 26:511 (1999), ACE inhibitors such as enalapril, cilazapril, enalaprilat, omapatrilat, lisinopril, rampril, captopril, furosemide, or trandopril, adrenomedullin, pyridoxalbenzoyl hydrozone analogs (U.S. Pat. No. 6,005,009), sulfonamidocarbonyl pyridine-2-carboxamides and pyridine-n-oxides, asporin, dextran sulfate, pentosan polysulfate, polysaccharides, HMG-CoA reductase inhibitors, e.g., statins, TGF-β receptor antagonists, β-adrenergic antagonists, e.g., β-receptor antagonists such as propanolol, metaprolol, carvediol, bunazosin, or isoprenaline, lacidipine, L-type/C-type calcium channel blockers, e.g., mibefradine, L-type calcium channel blockers, e.g., nifedipine, endothelin antagonists, such as endothelin A or B receptor inhibitors, e.g., BQ-123 or BQ788 (Higashi et al., *Br. J. Pharmacol.,* 121:782 (1997)), bosentan, as well as modulators of prolyl-4-hydroxylase (P4H), matrix metalloproteinases, TGF-β, PDGF, EGF, TGF-α, bFGF, IGF, IL-1, TNF-α, e.g., etanercept, catecholamines, steroids, retinoids, parathyroid hormones, or glucocorticoids, aldosterone, or antagonists thereof, e.g., spironolactone, bradykininase inhibitors, HOE 140 (Villareal et al., *Basic*

*Res. Cardiol.,* 93 Supp 3:4 (1998)), calcineurin modulators, e.g., calcineurin inhibitors, beta-blockers, bradykinin modulators, parathyroid hormone BB-94 (Bigatel et al., *J. Vasc. Surg.,* 29:130 (1999)), pentafluoro sulfanyl benzoyl guanidines, selective AT1 receptor antagonists, phenoxytoin, or modulators of endothelin, hydralazine, ramipril, furosemide, a calcium channel blocker, e.g., amlodipine, statins, propranolol, metaprolol, bunazosin, omapatrilat, isoproterenol, spirolactone, bradykinase inhibitors, chymase inhibitors, adriamycin, adrenomedullin, IL-6R inhibitors, cytokinases, chymase inhibitors, e.g., NK3201 (Sukenaga et al., *Jap. J. Pharmacol.,* 90:218 (2002)), adriamycin, phenyloin, tanshinone VI (Yagi, *J. Pharm. Soc. Japan,* 123:517 (2003), SB203680 (Akiyama-Uchida et al., *Hypertension,* 40:148 (2002), or a calcineurin inhibitor, e.g., FK506, or any combination thereof.

Other drugs within the scope of the invention include but are not limited to those useful to inhibit or treat neurodegenerative diseases such as cholinesterase inhibitors, olanzapine, aricept, anti-oxidants, e.g. coenzyme Q10, cholesterol lowering drugs, inhibitors of glutamate, e.g., Riluzole®, and antibiotics such as penicillin.

In one embodiment, a protein for use in the systems and methods of the invention includes but is not limited to a cytokine, e.g., a cytokine including but not limited to, γIP10, 4-1BBL, 6Ckine, activin, amphiregulan, angiostatin, Apo2L, APRIL, BAFF, ENA-78, eotaxin-1, eotaxin-2, eotaxin-3, EGF, FGF, e.g., bFGF, FGF-8b or FGF-2, FasL, G-CSF, GM-CSF, Gro-α, Gro-β, Gro-γ, HGF, HCC-1, HCC-4, HGF, IFNα, IFNβ, IGF-I, IGF-II, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, LARC, MCP-1, MCP-2, MCP-3, MCP-4, MCP-5, MEC, MIF, MIG, MIP1α, MIP1β, NGF, PIGF, PDGF, RANTES, SCF, SDF-1, TARC, P4H, TGF-α, TGF-β, TNF-α, TPO, e.g. VEGF such as VEGF-E (Kibu et al., *BBRC,* 301:371 (2003)), VEGF$_{165}$, or VEGF$_{121}$, NOS, angiopoietins, 12-LOX, IGF, matrix metallo-proteinases (MMPs) such as MMP-1, 2, 9 or 13, AT1 receptor antagonists such as leukemia inhibitor factor (LIF), cyclin D2, IGF, EGF, G-CSF, GMCSF, HGF, proliferin, and angiotropin, angiopoietins, e.g., Ang-1, PlGF (placental GF), decorin, or tissue inhibitor of metalloproteinase (TIMP).

Proteins useful to inhibit or treat neurodegenerative diseases include but are not limited to torsin, nerve growth factor, insulin like growth factor, etc.

Agents useful to treat diabetes include insulin, e.g., Navilog, Humalog, Humulin N, Humulin U, Lantus, Diabinesis, Amaryl, Glucotol, DiabBeta, Starlix, and pancreatic beta cells.

Donor cells within the scope of the invention include but are not limited to bone marrow-derived cells, e.g., mesenchymal cells and stromal cells, smooth muscle cells, fibroblasts, SP cells, pluripotent cells or totipotent cells, e.g., teratoma cells, hematopoietic stem cells, for instance, cells from cord blood and isolated CD34$^+$ cells, multipotent adult progenitor cells, adult stem cells, embryonic stem cells, skeletal muscle derived cells, for instance, skeletal muscle cells and skeletal myoblasts, cardiac derived cells, myocytes, e.g., ventricular myocytes, atrial myocytes, SA nodal myocytes, AV nodal myocytes, and Purkinje cells. The term "donor cell" includes embryonic, fetal, pediatric, or adult cells or tissues, including but not limited to, stem cells, precursors cells, and progenitor cells. Thus, donor cells of the invention can be myocardial cells, bone marrow cells, hematopoictic cells, lymphocytes, leukocytes, granulocytes, hepatocytes, monocytes, macrophages, fibroblasts, neural cells, mesenchymal stem cells, beta-islet cells, and combinations thereof, or cells capable of differentiating into those cells. In one embodiment, the donor cells are autologous cells, however, non-autologous cells, e.g., xenogeneic cells, may also be employed. In one embodiment, the donor cells are endothelial progenitor cells, CD133$^+$ cells, CD34$^+$ cells, mesenchymal stem cells, skeletal myoblasts, neural stem cells, pancreatic beta cells, cardiac stem cells or embryonic stem cells. Donor cells can be expanded in vitro to provide an expanded population of donor cells for administration.

In addition, donor cells may be treated in vitro to induce certain phenotypic characteristics, e.g., to induce proliferation or differentiation, to introduce one or more expression cassettes (transgenes) encoding a gene product, i.e., the donor cells may be recombinant cells. The expression cassette optionally includes at least one control element such as a promoter, optionally a constitutive promoter, an enhancer, or a transcription termination sequence. In one embodiment, a promoter is operably linked to an open reading frame encoding a force responsive gene product. Thus, the methods and systems of the invention include the use of recombinant cells as donor cells, which recombinant cells are force responsive as a result of expression of a recombinant force responsive gene product.

Preferably, the promoter and/or enhancer is one which is cell- or tissue-specific, e.g., cardiac cell-specific. For instance, the enhancer may be a muscle creatine kinase (mck) enhancer, and the promoter may be an alpha-myosin heavy chain (MyHC) or beta-MyHC promoter (see Palermo et al., *Circ. Res.,* 78, 504 (1996)).

Delivery of exogenous transgenes may be accomplished by any means, e.g., transfection with naked DNA, e.g., a vector comprising the transgene, liposomes, calcium-mediated transformation, electroporation, or transduction, e.g., using recombinant viruses. A number of transfection techniques are generally known in the art. See, e.g., Graham et al., *Virology,* 52, 456 (1973), Sambrook et al., *Molecular Cloning: A Laboratory Manual,* Cold Spring Harbor Laboratories, New York (1989), Davis et al., *Basic Methods in Molecular Biology,* Elsevier (1986) and Chu et al., *Gene,* 13, 197 (1981). Particularly suitable transfection methods include calcium phosphate co-precipitation (Graham et al., *Virol.,* 52, 456 (1973)), direct microinjection into cultured cells (Capecchi, *Cell,* 22, 479 (1980)), electroporation (Shigekawa et al., *BioTechniques,* 6, 742 (1988)), liposome-mediated gene transfer (Mannino et al., *BioTechniques,* 6, 682 (1988)), lipid-mediated transduction (Felgner et al., *Proc. Natl. Acad. Sci. USA,* 84, 7413 (1987)), and nucleic acid delivery using high-velocity microprojectiles (Klein et al., *Nature,* 327, 70 (1987)). Gene delivery vectors include, but are not limited to, isolated nucleic acid, e.g., plasmid-based vectors which may be extrachromosomally maintained, and viral vectors, e.g., recombinant adenovirus, retrovirus, lentivirus, herpesvirus including cytomegalovirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes.

The present agents may be employed with other agents including but not limited to diuretics such as thiazides, e.g., hydrochlorothizide, loop diuretics, e.g., furosemide, and potassium-sparing agents, e.g., amiloride, spironolactone and triamterene and hydrochlorothiazide, beta-blockers such as bisoprolol, carvedilol, labetolol and metoprolol, angiotensin-converting enzyme inhibitors such as benazepril, captopril, enalapril, fosinopril, lisinopril, perindopril, quinapril, ramipril, trandolapril, delapril, pentopril, moexipril, spirapril, temocapril, and imidapril, calcium channel blockers, alpha blockers, angiotensin II antagonists, e.g., losartan, statins, e.g., atorvastatin, pitavastatin, and pravastatin, or other lipid lowering agents, moxonidine, dihydropyridines, e.g., amlodipine, class III and IV antiarrhythmics, e.g., amiodarone, azimilide, sotalol, dofetilide, and ubutilide, aspirin, selective non-adrenergic imidazoline receptor inhibitors, hebivolol, vasopeptidase inhibitors, e.g., fasidotritat, omapatrilat, samapatrilat, substrates, inhibitors or inducers of cytochrome P450 enzymes, lidocaine, warfarin, oligonucleotides (sense or antisense), natriuretic peptides such as ANP, BNP, NT pro BNP, CNP, and DNP, colforsin daropate hydrochloride (forskilin derivative), antagonists of platelet integrin IIb/IIIa receptors, e.g., abciximab and trofiblant, reteplase, P2 receptor antagonists, e.g., ticlopidine and clopidrogel, mibefradil, hirudin, acetylcholinesterase inhibitors, cardiac glycosides, e.g., digoxin and digitoxin, bradykinin, neutral endopeptidase inhibitors, e.g., neprilysin, direct-acting vasodilators, e.g., hydralazine, nitroglycerin, sodium nitroprusside, catecholamines, dobutramine, dopamine, phosphodiesterase inhibitors, e.g., amrinone and milrinone, TNFα, pentoxifylline, growth hormone, cytokine inhibitors, aldosterone receptor antagonists, calcium sensitizers, nesiritide, 3,5-dicodothyropropionic acid, etomoxir, endothelin receptor antagonists, chlorthiadone, doxazosin, nesiritide, cilostazol, rilmenidine, ticlopidine, dihydropines such as nifedipine and nisoldipine, timolol, propanolol, verapamil, diltiazem, lisinopril, noopept (N-phenylacetyl-L-polyglycine ethylester), cariporide, geldanamycin, radicicol, ibudilast, selective delta (1) agonists such as 2-methyl-4a-alpha-(3-hydroxyphenyl)-1,2,3,4,4a,5,12,12a-alpha-octahydroquinolinol[2,3,3-g]isoquinoline, monophosphoryl lipid A, RC552, adenosine, adenosine receptor agonists, adenosine triphosphate sensitive channel openers, dipyridamole, fibroblast growth factor, atenolol, ezetimibe, lerosimendan, sirolimus, paclitaxil, actinomycin D, dexamethasone, tacrolimus, everolimus, estradiol, quinapril, tranilast, antiopeptin, trapidil, lacidipine, thiazolidinediones, fenofibrate, lacidipine, nebrivolol, nicotinic acid, probucal, rosuvastatin, gemfibrozil, glitazones, indobugen, alpha-tocopherol, dypiridamole, resins, e.g., cholestyramine and colestipol, bezafibrate, or listat, niacin, heparin, e.g., low molecular weight heparins such as dalteparin sodium and nadroparin calcium, bivalirucin, nitroglycerin, nicorandil, denopamine, eptifibatide, xemilofiban, bofiban, trimetazidine, nicorandil, dalteparin, and isosorbide 5-mononitrate. Additional pharmaceutical agents may be considered based on evidence of their direct or indirect roles in preventing or reducing injury or hemodynamic compromise related to myocardial infarction and/or heart failure. Examples of such pharmaceutical agents include, but are not limited to, L-arginine; nitric oxide (NO); NO derivatives such as nitroxl anion (HNONO—) and peroxynitrite (ONOO—); iNOS, eNOS, and inhibitors such as nitro-L-arginine methyl ester; NO donors such as diethylamine (DEA) NO and nitroglycerin (NTG); and interleukins and interleukin inhibitors.

Exemplary Complexes Useful to Label Therapeutic Agents

To "label" a therapeutic agent of the invention, a moiety, or a complex of molecules containing a moiety, that is responsive to a magnetic field, such as magnetic, paramagnetic and superparamagnetic particles, which preferably display no residual magnetism, is associated with, e.g., covalently attached to or having a noncovalent association with, a therapeutic agent. In one embodiment, the moiety or a complex of molecules containing the moiety that is responsive to a magnetic field, is covalently linked (conjugated to) isolated protein or drug. In one embodiment, the complex includes a targeting moiety that binds, e.g., noncovalently, to one or more specific ligands. For instance, a metal is covalently linked to an antibody specific for a therapeutic protein or an antibody specific for a therapeutic protein is associated with a metal bead. In another embodiment, a metal is covalently linked to an antibody specific for a cell surface molecule or another ligand or an antibody specific for a cell surface molecule or another ligand is associated with a metal bead, which is useful to label a cell having the cell surface molecule or label a ligand which is a drug. Targeting moieties or their ligands include, but are not limited to, polypeptides, nucleic acids, carbohydrates, lipids, hormones including proteinaceous and steroid hormones, growth factors, receptors, antibodies, and the like.

Thus, in one embodiment, the targeting moiety is an antibody. The term "antibody" includes antibody fragments, as are known in the art, including Fab, $Fab_2$, single chain antibodies (Fv for example), chimeric antibodies, etc., either produced by the modification of whole antibodies or those synthesized de novo using recombinant DNA technologies.

In a preferred embodiment, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', F(ab")2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature,* 321:522 (1986); Riechmann et al., *Nature,* 332:323 (1988); and Presta, *Curr. Op. Struct. Biol.,* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522 (1986); Riechmann et al., *Nature,* 332:323 (1988); Verhoeyen et al., *Science,* 239:1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, *J. Mol. Biol.,* 227:381 (1991); Marks et al., *J. Mol. Biol.,* 222:581 (1991)). The techniques of Cole et al. and Boerner et al. are also available for the preparation of human monoclonal antibodies (Cole et al., *Monoclonal Antibodies and Cancer Therapy,* Alan R. Liss, p. 77 (1985) and Boerner et al., *J. Immunol.,* 147:86 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature,* 368:856 (1994); Morrison, *Nature,* 368:812 (1994); Fishwild et al., *Nature Biotechnology,* 14:845 (1996); Neuberger, *Nature Biotechnology,* 14:826 (1996); Lonberg and Huszar, *Intern. Rev. Immunol.,* 13:65 (1995).

In one embodiment, the complex includes a targeting moiety such as an antibody specific for fetal liver kinase-1 (Flk1), smooth muscle cell-specific myosin heavy chain, vascular endothelial cell cadherin, bone-specific alkaline phosphatase (BAP), osteocalcin (OC), bone morphogenetic protein receptor (BMPR), CD4, CD8, CD34, CD34$^+$Sca1$^+$Lin$^-$, CD38, CD44, c-Kit, stem cell factor (SCF), leukocyte common antigen (CD45), lineage surface antigen (Lin), Mac-1, Muc-18 (CD146), stem cell antigen (Sca-1), stro-1 antigen, Thy-1, collagen type II, collagen type IV, keratin, sulfated proteoglycan, adipocyte lipid-binding protein (ALBP), fatty acid transporter (FAT), adipocyte lipid-binding protein (ALBP), albumin, B-1 integrin, CD133, glial fibrillary acidic protein (GFAP), microtubule-associated protein-2 (MAP-2), myelin basic protein (MPB), nestin, neural tubulin, neurofilament (NF), noggin, O4, O1, synaptophysin, tau, cytokeratin 19 (CK19), glucagon, insulin, insulin-promoting factor-1 (PDX-1), pancreatic polypeptide, somatostatin, alkaline phosphatase, alpha-fetoprotein (AFP), bone morphogenetic protein-4, brachyury, cluster designation 30 (CD30), cripto (TDGF-1), GATA-4, GCTM-2, genesis, germ cell nuclear factor, hepatocyte nuclear factor-4, neuronal cell-adhesion molecule, Oct-4, Pax6, stage-specific embryonic antigen-3, stage-specific embryonic antigen-4, telomerase, TRA-1-60, TRA-1-81, vimentin, MyoD, Pax7, myogenin, MR4, myosin heavy chain, and myosin light chain.

In one embodiment, the complex includes a targeting moiety such as an anti-Sca-1 or anti-c-Kit antibody linked to a metal or metal containing complex, e.g., a ferrous microbead, which may be contacted with stem cells, yielding labeled stem cells. In another embodiment, the complex includes a targeting moiety such as an anti-IL-2 antibody linked to a metal or metal containing complex, e.g., a ferrous microbead, which is contacted with IL-2 (a therapeutic protein). The anti-IL-2 antibody is preferably one which does not interfere, or does not substantially interfere, with binding of IL-2 to its receptor.

In another embodiment, the targeting moiety is all or a portion (e.g., a binding portion) of a non-antibody based ligand for a cell surface receptor. Suitable ligands include, but are not limited to, all or a functional portion of the ligands that bind to a cell surface receptor such as insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leutinizing hormone, lipotropin, melanocyte-stimutating hormone, norepinephrine, parathyroid hormone, thyroid-stimulating hormone (TSH), vasopressin, enkephalins, seratonin, estradiol, progesterone, testosterone, cortisone, and glucocorticoids and the hormones listed above. Receptor ligands include ligands that bind to receptors such as cell surface receptors, which include hormones, lipids, proteins, glycoproteins, signal transducers, growth factors, cytokines, and others.

Thus, in one embodiment, to label cells ex vivo for use in the systems and methods of the invention, cells may be contacted with a complex having a metal or a complex having a metal and a targeting moiety specific for an intracellular or cell surface bound ligand. For instance, dextran-coated iron oxide nanoparticles may be covalently attached to an anti-transferrin receptor monoclonal antibody (mAb), which induces receptor-mediated endocytosis. Nanoparticles within the scope of the invention include but are not limited to those having diameters of about 5 to about 200 nm, e.g., about 10 to about 100 nm. For improved cellular magnetic labeling, these particles can be derivatized (Josephson et al., *Bioconj. Chem.,* 10:186 (1999); Lewin et al., *Nat. Biotechnol.,* 18:410 (2000)). Larger particles, such as iron microbeads (microbeads useful in the invention may be about 0.5 to about 1.5 μm in diameter) that are coated with or covalently linked to antibodies or other ligands may also be employed. Different magnetic beads are available from a number of sources, including for example, Dynal (Norway), Advanced Magnetics (Cambridge, Mass., U.S.A.), Immuncon (Philadelphia, U.S.A.), Immunotec (Marseilles, France), and Miltenyi Biotec GmbH (Germany).

Another class of magnetic labels that can achieve a high degree of intracellular magnetic labeling that is non-specific (not dependent on targeted membrane receptor binding) are paramagnetic dendrimers (Wiener et al., *Magn. Reson. Med.,* 31:1 (1994); Bulte et al., *Invest. Radiol.,* 33:841 (1998); Bryant et al., *J. Magn. Reson. Imaging,* 9:348 (1999)). Moreover, dendrimers may serve as a matrix for the encapsulation of ultra-small copper, palladium, and platinum metal particles (Zhao et al., *J. Am. Chem. Soc.,* 120:4877 (1998); Balogh et al., *J. Am. Chem. Soc.,* 120:7355 (1998); Zhao et al., *Angew. Chem. Int. Edn. Engl.,* 38:364 (1999)). Dendrimers have been employed to prepare dendrimer-encapsulated, superparamagnetic iron oxides. Superparamagnetic particles have magnetic moments that, because of the small crystal size, are unhindered by lattice orientation and therefore do not exhibit hysteresis. In an applied magnetic field, the freedom of the individual moments to align themselves along the field results in the formation of a single spin, with a net moment at least 4 orders of magnitude higher than a comparable ensemble of paramagnetic spins, creating an extremely large microscopic field gradient for dephasing nearby protons (Bulte et al., *Scientific and Clinical Applications of Magnetic Carriers,* 527 (Plenum Press, New York; 1997); Bulte et al., *Focus on*

Biotechnology, 7:197 (Kluwer Academic Publishers, Norwell, Mass. (2001)). Because dendrimers are known to have high affinity for cellular membranes and are very efficient transfection agents for a wide variety of mammalian cells (Kukowska-Latalla et al., *Proc. Natl. Acad. Sci. USA*, 93:4897 (1996); Tang et al., *Bioconj. Chem.*, 7:703 (1996); Plank et al., *Human Gene Ther.*, 7:1437 (1996); DeLong et al., *J. Pharm. Sci.*, 86:762 (1997)), they readily allow entry of superparamagnetic nanoparticles into cells. In one embodiment, cells may be labeled with the magnetodendrimer MD-100.

In one embodiment of the invention, the moiety or complex used to label a therapeutic agent may include transition metal oxides, sulfides, silicides and carbides, and may also include more than one transition metal. In one embodiment, the label includes ferrites with the general formula $MOFe_2O_3$ in which M can be Zn, Gd, V, Fe, In, Cu, Co, Mg. Examples of suitable transition metal oxides include, but are not limited to: $CrO_2$, $COFe_2O_4$, $CuFe_2O_4$, $Dy_3Fe_5O_{12}$, $DyFeO_3$, $ErFeO_3$, $Fe_5Gd_3O_{12}$, $Fe_5HO_3O_{12}$, $FeMnNiO_4$, $Fe_2O_3$, $\gamma\text{-}Fe_3O_4$ (magnetite), $\alpha\text{-}Fe_3O_4$ (hematite), $FeLaO_3$, $MgFe_2O_4$, $Fe_2MnO_4$, $MnO_2$, $Nd_2O_7Ti_2$, $Al_2Fe_18NiO_4$, $Fe_2Ni_{0.5}O_4Zn_{0.5}$, $Fe_2Ni_{0.4}Zn_{0.6}$, $Fe_2Ni_{0.8}Zn_{0.2}$, $NiO$, $Fe_2NiO_4$, $Fe_5O_{12}Sm_3$, $Ag_{0.5}Fe_{12}La_{0.5}O_{19}$, $Fe_5O_{12}Y_3$, and $FeO_3Y$. Oxides of two or more of the following metal ions can also be used: Al(+3), Ti(+4), V(+3), Mn(+2), Co(+2), Ni(+2), Mo(+5), Pd(+3), Ag(+1), Cd(+2), Gd(+3), Tb(+3), Dy(+3), Er(+3), Tm(+3) and Hg(+1).

In one embodiment, one or more moieties or complexes that display superparamagnetic properties may be utilized in accordance with the invention. Superparamagnetic metal oxides have a mean diameter of less than about 100 nm, e.g., less than about 0.5 nm, and superparamagnetic nanoparticles may be, about 5 to 200 nm, e.g., about 5 to 25 nm, in diameter, and include a crystalline superparamagnetic metal or metal oxide core surrounded by a biocompatible polymer. Examples of materials that display superparamagnetic properties include but are not limited to magnetite ($\gamma\text{-}Fe_3O_4$), and hematite ($\alpha\text{-}Fe_3O_4$).

Methods to covalently or noncovalently attach metals or metal containing complexes to, or coat or embed metal containing beads with, proteins and other molecules, are known to the art. See, e.g., U.S. Pat. Nos. 5,130,118, 5,217,704 and 6,117,982, and U.S. published applications 20050175584 and 20040220086. For instance, proteins and other molecules, e.g., a targeting moiety, may be covalently linked to a metal chelator, which, once metal is bound, yields a labeled protein or other molecule within the scope of invention.

Exemplary Preparation of Metallodendrimers Useful in the Systems and Methods of the Invention A metal ion containing material can be used as a starting material. The metal ion containing material is contacted or mixed with at least one dendrimer. The metal ion containing material/dendrimer mixture is subjected to oxidation or hydrolysis conditions leading to the formation of an oxide or oxyhydroxide of the metal atom in the metal ion containing material. In other words, the metal (oxyhydr)oxide is formed in situ in the presence of the dendrimer. According to certain embodiments, the reaction may be considered a "mineralization" since the resulting metal (oxyhydr)oxide may be a crystalline mineral. An oxidizing agent may be used for effecting the oxidation and/or hydrolysis. Deaerated starting materials may be employed.

The sequence for adding together the metal ion containing material, dendrimer and oxidizing agent may vary. For example, the metal ion containing material and the dendrimer may be first mixed together followed by the addition of the oxidizing agent or the metal ion containing material and the oxidizing agent may be added simultaneously to the dendrimer. The starting materials also may be added together over a relatively short time period such as about one minute or the addition may be more controlled for a longer time period. For example, the oxidizing agent may be added over a period of about 1 to about 60 minutes. A slower rate of addition appears to lead to the development of a more fully crystalline metal (oxyhydr)oxide particle.

The relative amounts of the metal ion containing material, dendrimer and oxidizing agent may vary. For example, the amount of metal ion containing material relative to the dendrimer may range from about 10 to about 200, preferably from about 100 to about 200, molar ratio of metal ion:dendrimer. According to one embodiment the oxidizing agent is added in an approximately stoichiornetric amount relative to the metal molar content of the metal ion containing material. The conditions of the reaction are sufficient to oxidize and/or hydrolyze a substantial portion of the metal ions in the metal ion containing material. For example, once the oxidizing agent is added to the reaction mixture, the reaction mixture may be heated at a temperature of at least about 50, preferably about 60° C. for about 10 to about 120, e.g., about 30 to about 60, minutes. The oxidation reaction may be limited to about 60 minutes or less. The pH of the reaction mixture also may be controlled in a range of about 8.0 to about 10.0, for example, about 8.5 to about 9.0. The oxidation/hydrolysis can be performed in an aqueous medium under anaerobic conditions. Alternatively, the oxidation/hydrolysis can be performed in an aqueous medium under ambient atmosphere such that the $0_2$ in the atmosphere acts as the oxidizing agent.

A metal ion containing material, dendrimer and oxidizing agent are mixed together under conditions to oxidize the metal ion containing material. Metal oxide particles begin to form initially and simultaneously bond to an external outer surface of the dendrimer molecule. The result is a metal oxide-dendrimer complex. The terminal carboxy groups may initially bind and sequester the metal ion, with the dendrimer acting as a nucleation site for iron oxide synthesis. Such an intermediate complex may have an average diameter of about 7 to about 12 nm. Individual dendrimer molecules may be approximately about 4 to about 5 nm in diameter (Tan et al., *Polymer*, 40:2537 (1999) and Nisato et al., *Macromolecules*, 32:5895 (1999)). Mineral particles may not be entrapped within the dendrimer but may grow from the dendrimer surface, or may be at least partially within the dendritic spherical architecture. A highly charged carboxylate interface of a carboxy terminated dendrimer provides a surface favorable for the stabilization of iron oxides.

In one embodiment, to prepare a metal oxide-dendrimer composition, in general, under anaerobic conditions, carboxy-terminated dendrimers (generation 4.5, commercially available from Dendritech) in 0.1 M NaCl buffer, pH=8.5, are mixed with $(NH_4)_2Fe(SO_4)_2 \cdot 6H_2O$ at a loading factor of 100 iron atoms per dendrimer molecule. The mixture is then oxidized with the 2 electron oxidant MC3NO to yield a homogeneous brown suspension. The suspension pH is maintained by H$^+$ titration in a pH-Stat experiment (Brinkmann 718). Following termination of the reaction, 35 mM sodium citrate is added to bind any non-bound or released Fe ions. The resulting aqueous suspensions (referred to as "MD-100") are further purified and concentrated by ultrafiltration (MW cut-off, 100 KDa) and extensive dialysis. In one embodiment, mineral analysis indicates a highly ordered inverse spinel magnemite- or magnetite-like structure, with a high saturation magnetization ($M_{sat}$) of 94 emu g/Fe, and no hysteresis at 300K. For comparison, the $M_{sat}$ of pure magnetite ($Fe_3O_4$)

and maghemite ($\gamma Fe_2O_3$) is 127.1 and 108.7 emu g/Fe, respectively; for MION-46L (a dextran-coated magnetic nanoparticle), the magnetization at 1.5 Tesla is 60-68 emu g/Fe.

Dendrimers have a three-dimensional architecture with a core, a branching unit region, and terminal groups located at the outer surface or periphery of the three dimensional architecture. Dendrimers can be spheroid-shaped, cylindrical or rod shaped, ellipsoid-shaped or mushroom-shaped. An example of such a dendrimer is a so-called "starburst" dendrimer having concentric dendritic tiers around an initiator core. Mixtures of different dendrimers may be utilized.

Examples of dendrimers that may be useful include those that have cores of ammonia or 1,4-diaminobutane such as poly(amidoamine) (PAMAM) or poly(propyleneimine) (PPI) dendrimers. PAMAM or PPI dendrimers may be modified by techniques known in the art to include specific Rinctional outer surface terminal groups other than amino or methyl ester (in the case of PAMAM). For example, the methyl ester groups of PAMAM may be converted to carboxyl groups via hydrolysis (see, e.g., U.S. Pat. No. 5,527,524). Dendrimers having carboxy, sulfono, sulfonato, phosphono and phosphonato functional groups, including the salts or esters thereof, as the outer surface terminal groups may be particularly useful for stabilization of metal oxide particles. Carboxy-terminated PAMAM dendrimers such as a sodium carboxylate salt or a methyl ester carboxylate are an example of a useful dendrimer. The dendrimers used may be aqueous solutions.

The metal ion containing material used as a starting material may be in the form of a metal salt. The metal atom in the metal ion containing materials may include transition or lanthanide metal ions. Illustrative transition or lanthanide metal ions include iron, cobalt, gadolinium, europium, and manganese. Particularly exemplary embodiments include as the starting materials the $NO_3^-$, $SO_4^{2-}$, $Cl^-$, $Br^-$, $I^-$, acetate or oxalate salts of transition or lanthanide metals. For example, useful ferrous or ferric ion-containing materials include $(NH_4)_2Fe(SO_4)$, $FeCl_2$ and $FeSO_4$. Mixtures of different metal ion containing materials may be utilized. In the case of a transition metal ion as the starting material, the transition metal ion is oxidized to its corresponding metal oxide. In the case of a lanthanide metal ion as the starting material, the lanthanide metal ion is oxidized to its corresponding metal oxyhydroxide.

Oxidizing agents that may be used in connection with the invention are those that will oxidize a metal ion to its higher oxidation state under the disclosed reaction conditions. Illustrative oxidizing agents include $(CH_3)_3NO$, $H_2O_2$, $KlO_3$, and $O_2$ Mixtures of different oxidizing agents may be utilized.

For example, aqueous suspensions of Au colloids of about 2 to about 3 nm in size may be prepared by in situ reduction of $HAuCl_4$ in the presence of poly(amidoamine) dendrimers (Garcia et al, *Anal. Chem.*, 71:256 (1991)). Another approach is to functionalize the terminal groups of dendrimers with a metal chelating agent that is then chelated to a metal ion (see, e.g., Winer et al., *Magn. Reson. Med.*, 31:1 (1994), and U.S. Pat. Nos. 5,714,166 and 5,527,524). For example, $Gd^{3+}$ ions may be added to a metal chelate-dendrimer conjugate (Weiner et al., *J. Magn. Reson. Imaging*, 9:348 (1999)). U.S. Pat. Nos. 5,714,166 and 5,527,524 describe chelation of ferric ions by a sodium propionate-terminated sixth generation poly(amidoamine) dendrimer.

Optionally, a metal chelating agent may be added to the reaction or product mixture to chelate with any non-oxidized metal ion containing material. The resulting chelated metal is then removed from the product mixture via known separation techniques such as dialysis, gel filtration, ultrafiltration or ion exchange. Thus, an aqueous suspension of a metal (oxyhydr) oxide-dendrimer complex is substantially free of any metal chelating agents. Preferably, the metal chelating agent is added after the oxidation has been completed as determined by monitoring of the pH and visible UV spectrum. Exemplary metal chelating agents include citrates, diethylenetriaminepentaacetic acid (DTPA), ethylenediaminetetraacetic acid (EDTA), and acetates. Mixtures of different metal chelating agents may be utilized.

Magnetic-responsive metal (oxyhydr)oxide particles may be paramagnetic, ferrimagnetic, superparamagnetic or antiferromagnetic. According to one embodiment, the metal oxide particles are superparamagnetic, particularly iron oxide superparamagnetic particles. Examples of such superparamagnetic iron oxide particles include magnetite and magnemite. These particles possess a large ferrimagnetic moment that, because of the small crystal size, is free to align with an applied magnetic field (i.e., there is no hysteresis). The aligned magnetization then creates microscopic field gradients that dephase nearby protons and shorten the T2 NMR relaxation time, over and beyond the usual dipole-dipole relaxation mechanism that affects both TI and T2 relaxation times.

Examples of superparamagnetic iron oxides include MION-46L (available from Harvard Medical School), Feridex® (commercially available from Berlex Laboratories, Inc. under license from Advanced Magnetic, Inc), Endorem® ferumoxides (commercially available from Guerbet Group), Clariscan® (commercially available from Nycomed Amersham), Resovist® (commercially available from Schering AG), Combidex® (commercially available from Advanced Magnetics), and Sinerem® (commercially available from Guerbet Group under license from Advanced Magnetics). MION-46L is a dextran-coated nanoparticle with a superparamagnetic magnemite- or magnetite-like inverse spine core structure. The core structure has a diameter of about 4.611.2 nm in diameter and the overall particle size (including the dextran coating) is about 8 to about 20 nm. Feridex® is a FDA-approved aqueous colloid of superparamagnetic iron oxide associated with dextran for intravenous administration. Resovist® consists of superparamagnetic iron oxide particles coated with carboxydextran.

Particle aggregation beyond a selected size can be reversibly induced by the application of a strong magnetic field. Upon removal of the magnetic field, complete and immediate suspension is restored. Such behavior is characteristic of a superparamagnetic material having no remnant magnetization.

The magnetic-responsive coated metal oxide particles include a metal oxide particle and a coating material that is in contact with the surface of the metal oxide particle. The metal oxide particles typically are coated with the coating material prior to mixing with an optional transfection agent (i.e., precoated metal oxide particles are mixed with the transfection agent).

The coating material may be in contact with the metal oxide particle surface via any type of chemical bonding and/or physical attractive force such as, for example, covalent bonding, ionic bonding, hydrogen bonding, colloidal mixtures or complexing.

Illustrative coating materials include polysaccharides, polyvinyl alcohols, polyacrylates, polystyrenes, and mixtures and copolymers thereof. According to a particular embodiment the coating material is a polysaccharide such as, for example, starch, cellulose, glycogen, dextran, and derivatives thereof.

Metal (oxyhdr)oxide-dendrimer compositions can be used as magnetic labels for cells. One particular embodiment includes contacting living cells with the metal (oxyhydr)oxide-dendrimer composition to render the cells responsive to a magnetic field in vivo. Such magnetically labeled cells may be prepared by simple incubation of cells with the metal (oxyhydr)oxide-dendrimer composition in cell culture. Suitable cell incubation techniques are well know. For example, a cell of interest can be cultured in a standard media that includes the iron oxide-dendrimer composition at a dose ranging from about 1 to about 100 µg Fe/ml, e.g., about 1 to about 25 µg Fe/ml including about 5 to about 25 µg Fe/ml. In one embodiment, cells may be magnetically labeled by simply adding MD-100 to a culture medium at concentrations of up to 25 µg Fe/ml and incubation periods of 1-2 days. Prussian Blue staining of magnetically tagged cells may be used to evaluate the degree of intracellular labeling, with the cytoplasm containing large numbers of iron-containing vesicles or endosomes.

The metal (oxyhydr)oxide-dendrimer composition may be internalized by a cell by binding to the cell surface with subsequent entrance into the cytoplasm. The metal (oxyhydr)oxide-dendrimer composition may be internalized by a cell via a non-specific membrane adsorption process with subsequent intracellular localization in endosomes.

Transfection agents are known and typically are used as carriers for introducing DNA into a cell and may be employed to introduce labels described herein, into a cell. The transfection agent may have sufficient molecular size so that it includes a plurality of binding sites for the cell membrane. Although the molecular size for specific transfection agents will vary, most transfection agents can have a molecular weight of at least about 1 kDa, particularly at least about 5 kDa, and more particularly at least about 10 kDa. Illustrative transfection agents include cationic polyaminoacids (e.g., polyallylalanines, poly-L-alanines, poly-L-arginines, poly-L-lysines, and copolymers thereof), spermidines, salmon sperm DNA, poly-L-ornithines, diethylaminoethyl-dextrans, cationic liposomes or lipids, non-liposomal lipids, dendrimers, polynucleotides, and mixtures thereof. Examples of dendrimer transfection agents include those dendrimers having a relatively high electrostatic charge due to (activated) amino and/or carboxyl terminal groups on the outside perimeter of the dendrimer molecule. Such dendrimers can be activated, for instance, by heating up to about 60° C. to selectively remove a portion of the peripheral tertiary amine terminal groups. PolyFec® transfection reagent and SuperFect® transfection reagent are examples of commercially available activated dendrimers (available from Qiagen GmbH, Hilden, Germany). A commercially available example of a cationic liposome formulation is LipofectAMINE PLUS reagent from Life Technologies, Inc. A commercially available example of a non-liposomal lipid is Effectene™ transfection reagent from Qiagen GmbH, Hilden, Germany.

When the magnetic responsive coated metal oxide particles are mixed with the transfection agent, the transfection agent may be associated with the surface of the magnetic responsive coated metal oxide particles via electrostatic attraction. Thus, according to one embodiment, the transfection agent does not chemically bond to, or modify, the coating material on the surface of the magnetic responsive metal oxide particles. The transfection agent has a net negative or positive electrostatic charge and the magnetic responsive coated metal oxide particles has an oppositely corresponding net negative or positive electrostatic charge. The differential between the net electrical charges should cause a sufficient physical attraction so that the magnetic-responsive metal oxide particles and the transfection agent molecules are in close proximity to each other to form "clusters" that are distributed substantially uniformly throughout the mixture.

When coated metal oxide particle/transfection agent mixture is utilized for intracellular labeling, the coated metal oxide particles and transfection agent may be mixed together in the presence of a cell culture medium. The specific cell culture medium is selected based on the appropriate medium for the desired cell line for labeling. Selection of appropriate cell culture media is well within the skill of the art. The pH of the coated metal oxide particle/transfection agent/cell culture buffered media may be about 6.5 to about 7.5

The mixing typically may be done at ambient room temperature and atmosphere. One benefit of the disclosed composition is that commercially available magnetic responsive coated metal oxide particles and transfection agents may be mixed together as received without any pre-treatment or additional ingredients (other than the cell culture medium). For example, further chemical modification of the coating on the coated metal oxide particles is not required. Furthermore, the mixing may be accomplished without the presence of an organic solvent. The amount of coated metal oxide particles mixed with the transfection agents should be sufficient to provide uptake of the coated metal oxide particles by the cell and may vary widely depending upon the particular transfection agent.

Polymers

Compositions having a therapeutic agent may also include at least one polymer. In one embodiment, the polymer is biocompatible. In one embodiment of the invention, the polymer or polymers either bear, or are capable of being functionalized to bear —COOH or —NH$_2$ groups. Such groups can be advantageous in that it can allow biomolecules to be attached to the surface of particles or other molecules in accordance with the invention.

An example of a polymer that may be utilized in the invention includes polymeric vinyl alcohol, or polyvinyl alcohol (PVOH), which is a polyhydroxy polymer having a polymethylene backbone with pendent hydroxy groups. PVOH is a water soluble synthetic resin.

Solutions of polyvinyl alcohol in water can be made with large quantities of lower alcoholic cosolvents and salt cosolutes. Polyvinyl alcohol can react with aldehydes to form acetals, can be reacted with acrylonitrile to form cyanoethyl groups, and can be reacted with ethylene and propylene oxide to form hydroxy alkaline groups. Polyvinyl alcohols can be readily crosslinked and can be borated to effect gelation.

Polymers for use in particles in accordance with the invention may also result from the polymerization or copolymerization of monomeric alpha, beta unsaturated carboxylic acid or monomeric esters of alpha, beta unsaturated carboxylic acid. Suitable monomers include those containing a carboxylic acid or carboxylate group as a functional group and include a vinyl monomer having a free carboxylic acid or carboxylate functional group.

In one embodiment, the polymer results from a carboxylic acid containing monomers comprising alpha, beta unsaturated carboxylic acids including methacrylic acid, acrylic acid, itaconic acid, iconatic acid, aconitic acid, cinnamic acid, crotonic acid, mesaconic acid, carboxyethyl acrylic acid, maleic acid, fumaric acid, 3-acrylamidopropanesulfonic acid, 2-acrylamido-2-methylpropanesulfonic acid, 3-acryloyloxypropanesulfonic acid, and the like. The carboxylic acid functional copolymer can contain other ethylenically unsaturated monomers compatible with the ethylenically unsaturated carboxylic acid containing monomers disclosed above. Such monomers include ethylene, propylene, isobutylene, vinyl chloride, vinyl acetate, styrene, chlorostyrene, and the like. Further, the polymers can contain hydrophilic ethylenically unsaturated monomers having amino groups, hydroxyl groups, ether groups, ester groups, and others.

Alternatively the carboxylic acid functional polymer can be a polysaccharide having pendent carboxylic acid groups. Examples of such polysaccharide carboxylic acid functional polymers include carboxymethyl cellulose and carboxylethyl cellulose, carboxymethyl starch and carboxyethyl starch, alginic acid and alginic acid derivatives, pectic acid or similar natural and synthetic carboxylic acid derivatives of a polysaccharide. Also useful in the synthesis of an acrylic copolymer for use in particles of the invention are esters of alpha, beta unsaturated carboxylic acid such as those mentioned above.

The alkyl esters may be selected from higher alkyl esters such as those of about 5-22 carbon atoms. Examples of $C_{5-22}$ compounds include hexyl, octyl, ethyl (hexyl), isodecyl, and lauryl, acrylates, and methacrylates and itaconates. Alkyl esters having branched as opposed to straight chain moieties are also useful as copolymers for use in particles of the invention.

An additional family of monomers which has been found useful in producing polymers for use in particles of the invention are polymeric ethylene oxide resins. Generally ethylene oxide has the formula: $H(OCH_2CH_2)_nOH$.

Polyethylene oxides are generally clear viscous liquids, or depending on molecular weight and moles of ethylene oxide, white solids which dissolve in water, forming transparent solutions. Polyethylene oxide is soluble in many organic solvents and readily soluble in aromatic hydrocarbons while only slightly soluble in aliphatic hydrocarbons. Polyethylene oxides are generally classified not only by moles of ethylene oxide present within the composition, but also by molecular weight.

Therapeutic agents may be encapsulated by, embedded in or coated on a biocompatible material. Biocompatible materials include polyacetic or polyglycolic acid and derivatives thereof, polyorthoesters, polyesters, polyurethanes, polyamino acids such as polylysine, lactic/glycolic acid copolymers, polyanhydrides and ion exchange resins such as sulfonated polytetrafluorethylene, polydimethyl siloxanes (silicone rubber) or combinations thereof.

Additionally, it is possible to construct biocompatible materials from natural proteins or materials which may be crosslinked using a crosslinking agent such as 1-ethyl-3-(3-dimethylamino-propyl)carbodiimide hydrochloride. Such natural materials include albumin, collagen, fibrin, alginate, extracellular matrix (ECM), e.g., xenogeneic ECM, hyaluronan, chitosan, gelatin, keratin, potato starch hydrolyzed for use in electrophoresis, and agar-agar (agarose).

In one embodiment, the material may include liposomes, a hydrogel, cyclodextrins, nanocapsules or microspheres. Thus, a biocompatible material includes synthetic polymers in the form of hydrogels or other porous materials, e.g., permeable configurations or morphologies, such as polyvinyl alcohol, polyvinylpyrrolidone and polyacrylamide, polyethylene oxide, poly(2-hydroxyethyl methacrylate); natural polymers such as gums and starches; synthetic elastomers such as silicone rubber, polyurethane rubber; and natural rubbers, and include poly[α(4-aminobutyl)]-1-glycolic acid, polyethylene oxide (Roy et al., *Mol. Ther.*, 7:401 (2003)), poly orthoesters (Heller et al., *Adv. Drug Delivery Rev.*, 54:1015 (2002)), silk-elastin-like polymers (Megeld et al., *Pharma. Res.*, 19:954 (2002)), alginate (Wee et al., *Adv. Drug Deliv. Rev.*, 31:267 (1998)), EVAc (poly(ethylene-co-vinyl acetate), microspheres such as poly(D, L-lactide-co-glycolide) copolymer and poly(L-lactide), poly(N-isopropylacrylamide)-b-poly(D,L-lactide), a soy matrix such as one crosslinked with glyoxal and reinforced with a bioactive filler, e.g., hydroxylapatite, poly(epsilon-caprolactone)-poly (ethylene glycol) copolymers, poly(acryloyl hydroxyethyl) starch, polylysine-polyethylene glycol, an agarose hydrogel, or a lipid microtubule-hydrogel.

In one embodiment, the biocompatible material includes but is not limited to hydrogels of poloxamers, polyacrylamide, poly(2-hydroxyethyl methacrylate), carboxyvinylpolymers (e.g., Carbopol 934, Goodrich Chemical Co.), cellulose derivatives, e.g., methylcellulose, cellulose acetate and hydroxypropyl cellulose, polyvinyl pyrrolidone or polyvinyl alcohols.

In some embodiments, the biocompatible polymeric material is a biodegradable polymeric such as collagen, fibrin, polylactic-polyglycolic acid, or a polyanhydride. Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D,L-lactide-co-glycolide) block copolymers, polyglycolide, polylactides (PLLA or PDLA), poly(caprolactone) (PCL), poly(dioxanone) (PPS) or cellulose derivatives such as cellulose acetate. In an alternative embodiment, a biologically derived polymer, such as protein, collagen, e.g., hydroxylated collagen, or fibrin, or polylactic-polyglycolic acid or a polyanhydride, is a suitable polymeric matrix material.

In another embodiment, the biocompatible material includes polyethyleneterephalate, polytetrafluoroethylene, copolymer of polyethylene oxide and polypropylene oxide, a combination of polyglycolic acid and polyhydroxyalkanoate, or gelatin, alginate, collagen, hydrogels, poly-3-hydroxybutyrate, poly-4-hydroxybutyrate, and polyhydroxyoctanoate, and polyacrylonitrilepolyvinylchlorides.

Other biocompatible materials include natural polymers such as starch, chitin, glycosaminoglycans, e.g., hyaluronic acid, dermatan sulfate and chrondrotin sulfate, collagen, and microbial polyesters, e.g., hydroxyalkanoates such as hydroxyvalerate and hydroxybutyrate copolymers, and synthetic polymers, e.g., poly(orthoesters) and polyanhydrides, and including homo and copolymers of glycolide and lactides (e.g., poly(L-lactide, poly(L-lactide-co-D,L-lactide), poly(L-lactide-co-glycolide, polyglycolide and poly(D,L-lactide), pol(D,L-lactide-coglycolide), poly(lactic acid colysine) and polycaprolactone. The incorporation of molecules such as tricalciumphosphate, hydroxyapetite and basic salts into a polymer matrix can alter the degradation and resorption kinetics of the matrix. Moreover, the properties of polymers can be modified using cross-linking agents.

In one embodiment, the biocompatible material is isolated ECM. ECM may be isolated from endothelial layers of various cell populations, tissues and/or organs, e.g., any organ or tissue source including the dermis of the skin, liver, alimentary, respiratory, intestinal, urinary or genital tracks of a warm blooded vertebrate. ECM employed in the invention may be from a combination of sources. Isolated ECM may be prepared as a sheet, in particulate form, gel form and the like. The preparation and use of isolated ECM in vivo is described in co-pending, commonly assigned U.S. patent application Ser. No. 11/017,237, entitled "USE OF EXTRACELLULAR MATRIX AND ELECTRICAL THERAPY," filed on Dec. 20, 2004, which is hereby incorporated by reference in its entirety.

Compositions, Dosages, Routes of Administration and Exemplary Field Strength

The amount of agent administered will vary depending on various factors including, but not limited to, the agent chosen, the disease, whether prevention or treatment is to be achieved. Thus, the agents of the invention may be employed in conjunction with other therapies. Administration of the agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms comprising the agents of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes, although local administration of at least one agent via an implantable device is a preferred embodiment of the invention. The formulations may, where appropriate, be conveniently presented in discrete unit dosage forms and may be prepared by any of the methods well known to pharmacy. Such methods may include the step of bringing into association the agent with liquid carriers, solid matrices, semi-solid carriers, finely divided solid carriers or combinations thereof, and then, if necessary, introducing or shaping the product into the desired delivery system.

Pharmaceutical formulations containing the agents of the invention can be prepared by procedures known in the art using well known and readily available ingredients. For example, the agent can be formulated with common excipients, diluents, or carriers. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols. The formulations can include buffering agents such as calcium carbonate, magnesium oxide and magnesium carbonate, as well as, inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and gelatin, microcrystalline cellulose, sodium lauryl sulfate, starch, talc, or titanium dioxide, or liquid vehicles such as polyethylene glycols (PEGs) and vegetable oil.

The pharmaceutical formulations of the agents of the invention can also take the form of an aqueous or anhydrous solution or dispersion, or alternatively the form of an emulsion or suspension.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

Additionally, the agents are well suited to formulation as sustained release dosage forms and the like. The coatings, envelopes, and protective matrices may be made, for example, from polymeric substances, such as polylactide-glycolates, liposomes, microemulsions, microparticles, nanoparticles, or waxes.

The formulations and compositions described herein may also contain other ingredients such as antimicrobial agents, or preservatives. Furthermore, as described herein the active ingredients may also be used in combination with other therapeutic agents.

The cells to be administered may be a population of individual cells or cells grown in culture so as to form a two dimensional or three dimensional structure. The number of cells to be administered will be an amount which results in a beneficial effect to the recipient. For example, from $10^2$ to $10^{10}$, e.g., from $10^3$ to $10^9$, $10^4$ to $10^8$, or $10^5$ to $10^7$, cells can be administered to, e.g., injected, the region of interest, for instance, infarcted and tissue surrounding infarcted tissue. The cells may be administered before, during or after a vascular procedure or an invasive or minimally invasive surgical procedure. Thus, transvascular methods may be employed, e.g., intracoronary infusion, intravenous infusion, or direct injection into tissue such as transendocardial injection, transepicardial injection or transcoronary vein injection. In one embodiment, the cells are administered post-MI, within hours, e.g., 1 to 12 hours, to days, e.g., 1 to 2 days, or one or more weeks after MI. Preferably, the administration of donor cells is prior to scar formation. The cells may be administered intravenously, transvenously, intramyocardially or by any other convenient route, and delivered by a needle, catheter, e.g., a catheter which includes an injection needle or infusion port, or other suitable device.

Useful field strengths may be found in *Scientific and Clinical Applications of Magnetic Carriers*, Eds Häfeli et al., Plenum Press, NY (1997), Chalmers et al., *Biotechnol. Bioeng.*, 59:10 (1998), Miltenyi, *Cytometry*, 11:231 (1990) and McCloskey et al., *Anal. Chem.*, 75:6868 (2003). The magnetic field application may be similar to that employed for high gradient magnetic separation (HGMS). HGMS systems are known in the art, see for example U.S. Pat. Nos. 4,452,773, 4,230,685, 4,770,183, 5,385,707, 5,411,863, 5,543,289, 5,693,539, 6,020,210, and 6,417,011, WO85/04330, and PCT/EP89/01602. The magnet may be sufficiently strong at the minimum to create a field of about 0.05 to about 4 Tesla, e.g., 0.5 to 1 Tesla.

Exemplary Devices

FIG. 1 is an illustration of an embodiment of a therapy delivery system including one or more magnetic field generating devices and portions of the environment in which the therapy system operates. As illustrated in FIG. 1, a heart 100 has an injured region 102. Injured region 102 may result from, for example, cardiac ischemia or myocardial infarction. To treat injured region 102 and restore normal function of heart 100, a therapeutic agent 104 is administrated into injured region 102 and/or its vicinity. Therapeutic agent 104 is associated with a complex which includes a force responsive moiety that is responsive to magnetic field. A magnetic field is applied to injured region 102 and/or its vicinity to enhance retention of therapeutic agent 104. To generate this magnetic field, one or more of magnetic field generating devices 120, 130, and 140 are used.

Magnetic field generating device 120 is an external magnetic field-generating device configured to be externally attached onto skin 110 of a patient over injured region 102. In various embodiments, depending on the duration of the magnetic field application, magnetic field generating device 120 can be held in place by a hand or a belt, or glued or taped onto skin 100. Examples of magnetic field generating device 120 include a magnet and an electromagnet. In one embodiment, magnetic field generating device 120 is incorporated into an adhesive pad for attachment onto skin 110.

Magnetic field generating device 130 is an implantable magnetic field-generating device configured to be placed on or near the epicardial surface of heart 100 over injured region 102. In various embodiments, magnetic field generating device 130 is directly affixed onto heart 100 or incorporated into another implantable device. Examples of magnetic field generating device 130 include a magnet and an electromagnet such as a solenoid. In one embodiment, magnetic field generating device 130 includes a magnet placed on or near the epicardial surface of heart 100 over injured region 102 by a minimally invasive operation, such as via a sub-exphoid approach. In another embodiment, magnetic field generating device 130 includes a magnet or magnet powder incorporated into an epicardial device such as an epicardial patch, an epicardial bulking agent, or an epicardial lead or catheter.

Magnetic field generating device 140 is an implantable magnetic field generating device configured to be placed in heart 100 near injured region 102. Examples of magnetic field generating device 140 include a magnet and an electromagnet. In one embodiment, magnetic field generating device 140 is incorporated into an intracardiac device such as a pacing or defibrillation lead, a guide wire, or a stylet, as further discussed below with reference to FIGS. 3-6.

In various embodiments, one or more of magnetic field generating devices 120, 130, and 140 are selected to apply the magnetic field. A physician may choose one of magnetic field generating devices 120, 130, and 140 based on considerations including the duration of magnetic field application and other therapies the patient receives. For example, magnetic field generating devices 120 may be chosen when the duration of the magnetic field application is short and/or when the patient does not otherwise need an implantable device. Magnetic field generating devices 130 may be chosen when an operation providing for access to heart 100 is performed for another reason and/or when an epicardial lead or catheter is introduced. Magnetic field generating devices 140 may be chosen when an endocardial lead is used to provide for electrical connection between an implantable device such as an implantable pacemaker or defibrillator and heart 100. In one embodiment, one of magnetic field generating devices 120, 130, and 140 is chosen at different stage of treatment for the patient. For example, magnetic field generating devices 120 may be used before the patient receives an implantable device. A guide wire or stylet including magnetic field generating devices 140 may be used during the implantation of the implantable device and at least one lead. The lead may include magnetic field generating devices 140 for use after the implantable device is implanted.

Figure 2:
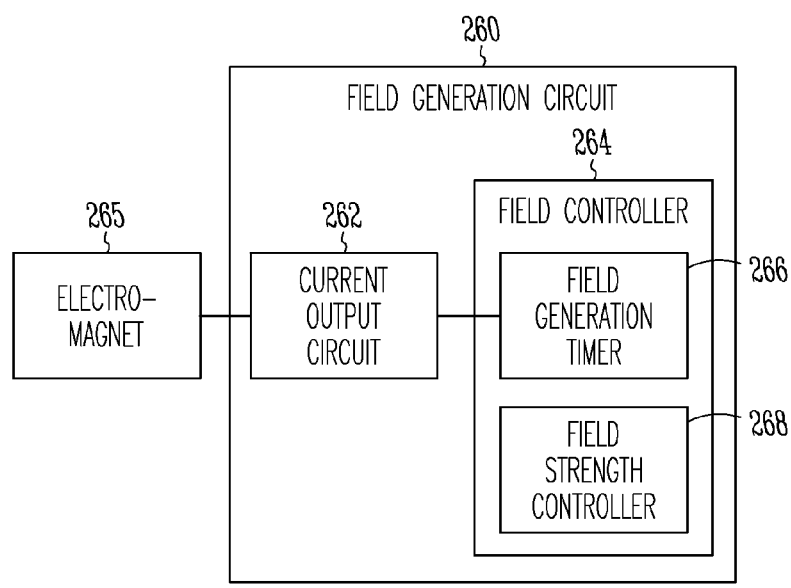
FIG. 2 is an illustration of an embodiment of a magnetic field generation system.

FIG. 2 is an illustration of an embodiment of a magnetic field generating system including an electromagnet 265 and a field generation circuit 260. Electromagnet 265 is a specific embodiment of magnetic field generating device 120, 130, or 140 and generates a magnetic field when an electric current follows through it. In one embodiment, the electromagnet is a solenoid. Field generation circuit 260 supplies that electric current. While a magnet provides for a simple magnetic field generating device, an electromagnet allows automatic control of timing and/or strength of the magnetic field.

Field generation circuit 260 includes a current output circuit 262 and a field controller 264. Current output circuit 262 delivers an electric current through electromagnet 265 to generate the magnetic field from electromagnet 265. Field controller 264 controls the generation of the magnetic field and includes a field generation timer 266 and a field strength controller 268. Field generation timer 266 times the generation of the magnetic filed. In various embodiments, the magnetic field is applied for one or more predetermined durations. During each of the predetermined durations, the magnetic field is applied continuously or intermittently (with a predetermined duty cycle). Field strength controller 268 controls the strength of the magnetic field by controlling the amplitude of the electric current delivered from current output circuit 262.

Figure 3:
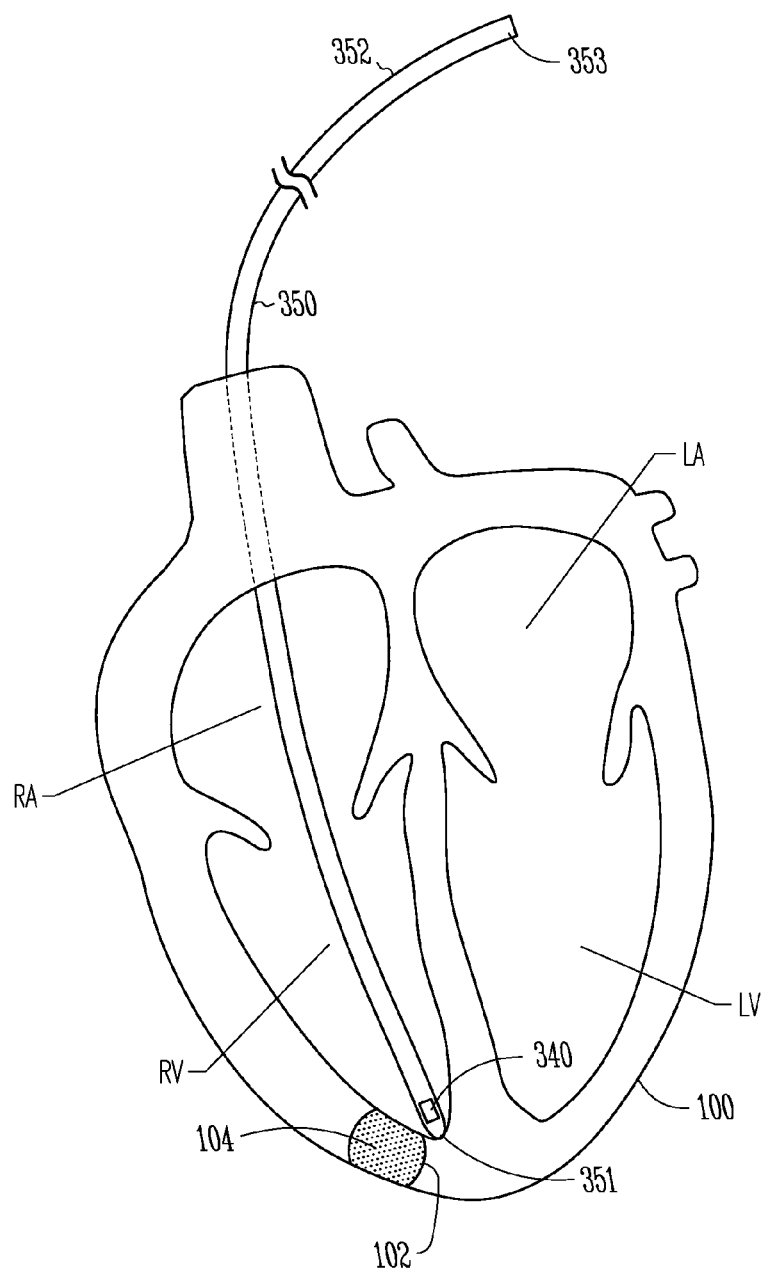
FIG. 3 is an illustration of an embodiment of an implantable lead including a magnetic field generating device and portions of the environment in which the lead is used.

FIG. 3 is an illustration of an embodiment of an implantable lead 350 and portions of the environment in which lead 350 is used. Lead 350 is an endocardial lead including a magnetic field generating device 340, which is a specific embodiment of magnetic field generating device 140.

Lead 350 has a proximal end 353, a distal end 351, and an elongate body 352 coupled between proximal end 353 and distal end 351. Distal end 351 is configured for endocardial placement in heart 100. In one embodiment, as illustrated in FIG. 3, distal end 351 includes magnetic field generating device 340. In one embodiment, proximal end 353 is configured to be connected to an implantable medical device. In a specific embodiment, magnetic field generating device 340 includes an electromagnet, and the implantable medical device includes field generation circuit 260, which is electrically connected to the electromagnet through electrical conductors extending through lead 350.

Figure 4:
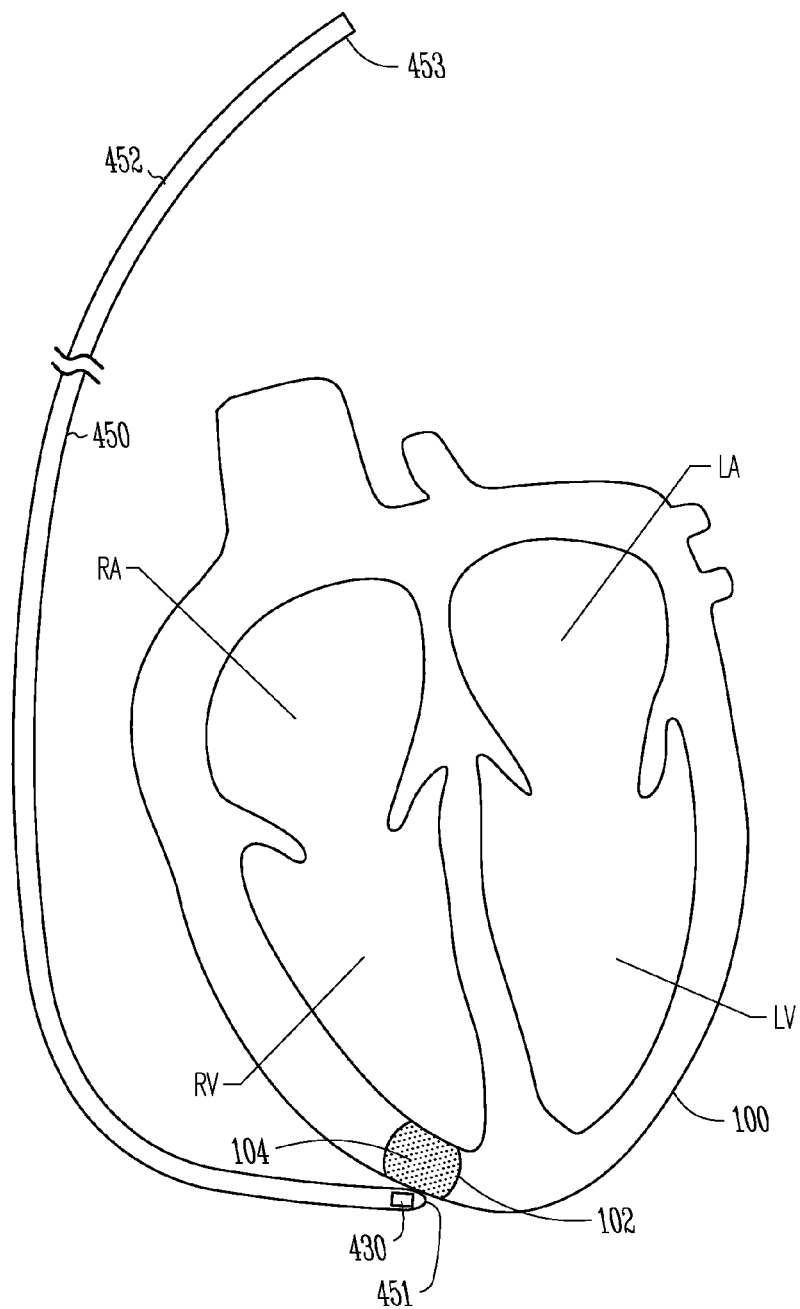
FIG. 4 is an illustration of an embodiment of another implantable lead including the magnetic field generating device and portions of the environment in which the lead is used.

FIG. 4 is an illustration of an embodiment of an implantable lead 450 and portions of the environment in which lead 450 is used. Lead 450 is an epicardial lead including a magnetic field generating device 430, which is a specific embodiment of magnetic field generating device 130.

Lead 450 has a proximal end 453, a distal end 451, and an elongate body 452 coupled between proximal end 453 and distal end 451. Distal end 451 is configured for epicardial placement on heart 100. In one embodiment, as illustrated in FIG. 4, distal end 451 includes magnetic field generating device 430. In one embodiment, proximal end 453 is configured to be connected to an implantable medical device. In a specific embodiment, magnetic field generating device 430 includes an electromagnet, and the implantable medical device includes field generation circuit 260, which is electrically connected to the electromagnet through electrical conductors extending through lead 450.

Figure 5:
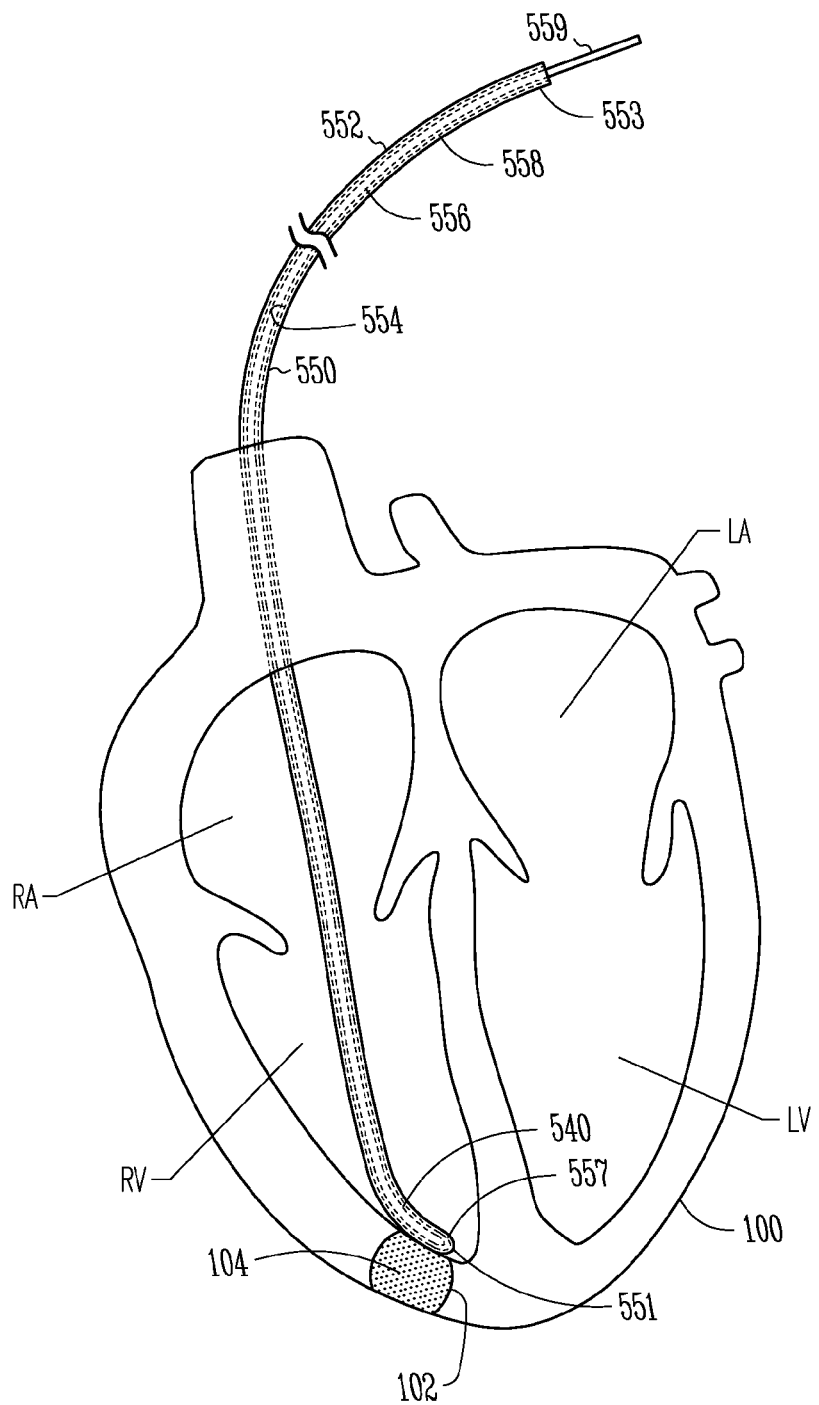
FIG. 5 is an illustration of an embodiment of an implantable lead accommodating portions of an elongate device including a magnetic field generating device and portions of the environment in which the lead is used.

FIG. 5 is an illustration of an embodiment of an implantable lead 550 accommodating portions of an elongate device 556 and the environment in which lead 550 is used.

Lead 550 has a proximal end 553, a distal end 551, an elongate body 552 coupled between proximal end 553 and distal end 551, and a lumen 554 extending within elongate body 552 from proximal end 553 to distal end 551. Lumen 554 accommodates at least a portion of elongate device 556. Elongate device 556 has a proximal end 559, a distal end 557, and a body 558. At least a portion of elongate device 556 is constructed with magnetic material to form magnetic field generating device 540. In one embodiment, the magnetic material includes a material embedded with magnet powder.

In one embodiment, as illustrated in FIG. 5, distal end 557 includes magnetic field-generating device 540.

In one embodiment, elongate device 556 is a guide wire. In another embodiment, elongate device 556 is a stylet.

Figure 6:
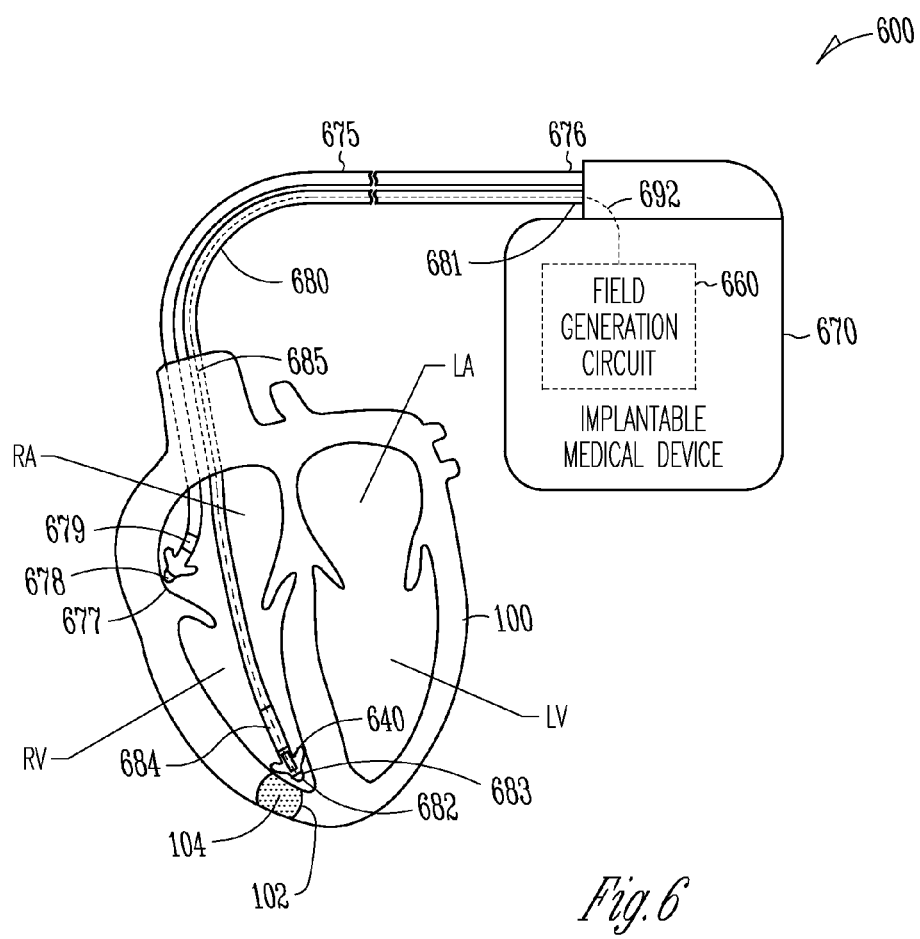
FIG. 6 is an illustration of an embodiment of an implantable cardiac rhythm management (CRM) system and portions of the environment in which the implantable CRM system operates.

FIG. 6 is an illustration of an embodiment of an implantable cardiac rhythm management (CRM) system 600 and portions of the environment in which the CRM system operates. System 600 includes an implantable medical device 670 that is electrically coupled to heart 100 through implantable leads 675 and 680.

In one embodiment, as illustrated in FIG. 6, implantable medical device 670 is an implantable cardioverter/defibrillator (ICD) with cardiac pacing capabilities. In another embodiment, in addition to a pacemaker and a cardioverter/defibrillator, implantable medical device 670 also includes one or more of other monitoring and/or therapeutic devices such as a neural stimulator, a drug delivery device, and a biological therapy device. Implantable medical device 670 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 6, the electronic circuit senses at least an atrial electrogram and a ventricular electrogram from heart 100 and delivers pacing and cardioversion/defibrillation pulses to heart 100. Lead 675 is a pacing lead that includes a proximal end 676 connected to implantable medical device 670 and a distal end 677 placed in the right atrium (RA) of heart 100. A pacing-sensing electrode 678 (referred to as the "RA tip" electrode) is located at distal end 677. Another pacing-sensing electrode 679 (referred to as the "RA ring" electrode) is located near distal end 677. Electrodes 678 and 679 are electronically connected to implantable medical device 670 via separate conductors in lead 675 to allow sensing of an atrial electrogram and/or delivery of atrial pacing pulses. Lead 680 is a defibrillation lead that includes a proximal end 681 connected to implantable medical device 670 and a distal end 682 placed in the right ventricle (RV) of heart 100. A pacing-sensing electrode 683 (referred to as the "RV tip" electrode) is located at distal end 682. A defibrillation electrode 684 (referred to as the "RV coil" electrode) is located near distal end 682 but electrically separated from pacing-sensing electrode 683. Another defibrillation electrode 685 (referred to as the "SVC coil" electrode) is located at a distance from distal end 682 for placement in the superior vena cava (SVC). In one embodiment, electrode 685 is electrically connected to the hermetically sealed can. Electrodes 683, 684, and 685 are electrically connected to implantable medical device 670 via separate conductors in lead 680. Electrode 683 allows sensing of a ventricular electrogram and/or delivery of ventricular pacing pulses. Electrodes 684 and 685 allow sensing of a ventricular electrogram and/or delivery of ventricular cardioversion/defibrillation pulses.

As illustrated in FIG. 6, lead 680 is a specific embodiment of lead 350 and includes a magnetic field generating device 640. In one embodiment, as illustrated in FIG. 6, magnetic field generating device 640 includes a electromagnet incorporated into distal end 682, and implantable medical device 670 includes a field generation circuit 660 connected to the electromagnet via electrical conductors 692. A specific embodiment of field generation circuit 660 is illustrated in FIG. 2 as field generation circuit 260. In another embodiment, magnetic field generating device 640 includes a magnet.

Without magnetic field generating device 640 and electrical conductors 692, lead 680 also represents a specific embodiment of lead 550. In one embodiment, elongate device 556 is used to apply the magnetic field during the implant of lead 680, which includes a lumen that accommodates at least a portion of elongate device 556 and allows magnetic field generating device 540 to apply the magnetic field to injured region 102.

In various embodiments, one or more magnetic field generating devices are incorporated into one or more leads of system 600 or a CRM system similar to system 600. In one embodiment, a magnetic field generating device is incorporated into the distal end of a lead intended to be placed near the cardiac region to be treated. In another embodiment, one or more magnetic field generating devices are incorporated into a lead along its elongate body, such that at least one magnetic field generating device can be placed near the cardiac region to be treated.

Exemplary Methods of the Invention

The invention provides methods of labeling a cell, protein or drug with at least one field responsive moiety optionally including at least one polymer and/or a targeting moiety, and methods of localizing the labeled cell, protein or drug in a mammal by employing an implantable or external device.

In one embodiment, labeling a cell with a particle in accordance with the invention includes the uptake of the particle by the cell. The particle can be taken into the cell through a number of different processes, including but not limited to, phagocytosis, endocytosis or microinjection. In one embodiment of the invention, the mechanism of the incorporation of particles into cells includes nonspecific phagocytosis. The structure of the particle itself can enhance the uptake of the particle by the cell. For example, the surface of the particle can be modified so that it is a better candidate for phagocytosis or endocytosis. One example of a surface modification includes attachment of a specific antibody to a cell surface protein that may promote endocytosis. In one embodiment of the invention, particles in accordance with the invention are taken up very rapidly and with high efficiency into the cells, with no apparent toxicity or impact on bioactivity, despite dense loading of the cells with the particles.

Furthermore, particles in accordance with the invention can create a much greater magnetic moment within individual cells, increasing the likelihood that in vivo localization of very small numbers of cells is possible.

In one embodiment, a mammal in need of cardiac cell therapy such as a mammal post-MI is administered labeled donor cells. Cells, for instance, stem cells, to be transplanted are magnetically tagged by incubation with a magnetodendrimer for 1 to 2 days, or mixed with an antibody that binds cell surface molecules (e.g., Sca-1 or c-Kit) which antibody is coupled to a magnetic bead. Cells are administered, for instance, using a coronary artery guide catheter or lumen of a balloon catheter, or directly injected into the epicardium or endocardium with a non-magnetic needle. A magnetic field may be introduced in a closed-chest application. For instance, application of a magnetic field over the infarct area then supplies an additional external force to temporarily improve cell retention.

In one embodiment, a guide wire is constructed with a permanent magnet (e.g., magnet powder) and placed in an infarct area via a coronary artery or vein. In another embodiment, a lead, for instance, a pacing lead, having a permanent or temporary magnet (e.g., electromagnet) at the distal end is placed peri-infarct (at or near the infarct area). After injection of magnetically labeled cells, a current is applied to the electromagnet to generate a magnetic field. The field may be applied for a variable duration to provide additional forces that encourage cell retention. Alternatively, a stylet with a permanent magnet may be inserted into the lead to produce the magnetic field. In a minimally invasive application, a magnet may be applied to the epicardium (e.g., via a sub-xyphoid approach) and allowed to remain in place for a period of time effective to enhance therapeutic agent concentration. The magnet may be an electromagnet or a permanent magnet. Thus, devices may be independent of the method of cell administration and may be especially advantageous for IV injections of cells where cell retention in the infarct area is poor.

In another embodiment, a mammal having liver damage is administered liver cells magnetically tagged by incubation with a magnetodendrimer or mixed with an antibody that binds liver cell surface molecules which antibody is coupled to a magnetic bead directly to the liver or intravenously. Application of an external magnetic field over the liver improves donor liver cell retention.

In yet another embodiment, a mammal having a localized neurodegenerative disorder is administered NGF embedded in a ferrous microbead. Application of a magnetic field near the area having neurodegeneration increases the concentration of NGF, which may induce nerve regeneration.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is

1. A method to enhance the efficacy of engraftment of cells, comprising:

administering to a mammal in need of therapy a composition comprising donor cells for engraftment to an injured region which cells are associated with a complex which comprises a force responsive moiety that is responsive to a magnetic field; and applying a magnetic field to the mammal from an implantable magnetic field generating device in the mammal, which device is on the epicardium near the injured region, in an amount and for a time effective to increase the engraftment of the cells at the injured region, wherein the implantable magnetic field generating device is coupled to an implantable medical device including a field controller adapted to control the generation of the magnetic field which includes a field generation timer adapted to time one or more predetermined durations during which the magnetic field is generated with a predetermined duty cycle.

2. The method of claim 1 wherein the donor cells comprise magnetic nanoparticles.

3. The method of claim 1 wherein the donor cells are bound to antibodies comprising the force responsive moiety.

4. The method of claim 1 wherein the donor cells comprise stem cells.

5. The method of claim 1 wherein the force responsive moiety comprises a metal.

6. The method of claim 1 wherein the complex comprises an antibody.

7. The method of claim 6 wherein the antibody binds Sca-1 or c-Kit.

8. The method of claim 1 wherein the composition comprises a liposome.

9. The method of claim 1 wherein the composition comprises a force responsive moiety that is a magnetodendrimer.

10. The method of claim 1 wherein the complex comprises a nanoparticle.

11. The method of claim 1 wherein the complex comprises a cell surface receptor ligand.

12. The method of claim 1 wherein the donor cells comprise an expression cassette comprising a promoter operably linked to an open reading frame encoding a force responsive gene product.

* * * * *